(12) United States Patent
Rossi

(10) Patent No.: US 10,458,833 B2
(45) Date of Patent: Oct. 29, 2019

(54) BLOOD RESERVOIR WITH FLUID VOLUME MEASUREMENT BASED ON PRESSURE SENSOR

(71) Applicant: Sorin Group Italia S.r.l., Milan (IT)

(72) Inventor: Ivan Rossi, Poggio Rusco (IT)

(73) Assignee: Sorin Group Italia S.r.l., Milan (IT)

( * ) Notice: Subject to any disclaimer, the term of this patent is extended or adjusted under 35 U.S.C. 154(b) by 162 days.

(21) Appl. No.: 15/311,495

(22) PCT Filed: May 16, 2014

(86) PCT No.: PCT/IB2014/061491
§ 371 (c)(1),
(2) Date: Nov. 15, 2016

(87) PCT Pub. No.: WO2015/173611
PCT Pub. Date: Nov. 19, 2015

(65) Prior Publication Data
US 2017/0089746 A1    Mar. 30, 2017

(51) Int. Cl.
*G01F 23/14* (2006.01)
*A61M 1/36* (2006.01)
*A61M 1/02* (2006.01)

(52) U.S. Cl.
CPC ............ *G01F 23/14* (2013.01); *A61M 1/024* (2013.01); *A61M 1/3627* (2013.01);
(Continued)

(58) Field of Classification Search
CPC .. A61M 1/024; A61M 1/3627; A61M 1/3666; A61M 1/3693; A61M 2205/3331;
(Continued)

(56) References Cited

U.S. PATENT DOCUMENTS 3,551,072 A    12/1970   Zimmerly
3,588,589 A     6/1971   Emmasingel
(Continued)

FOREIGN PATENT DOCUMENTS

CN    86103696 A    1/1987
CN     1147964 A    4/1997
(Continued)

OTHER PUBLICATIONS

Catalog of Products, 2009 Terumo Europe Cardiovascular Systems, 142 pages.
(Continued)

*Primary Examiner* — Randy W Gibson
*Assistant Examiner* — Gedeon M Kidanu
(74) *Attorney, Agent, or Firm* — Faegre Baker Daniels LLP

(57) ABSTRACT

A system includes a fluid reservoir, a differential pressure sensor, and a controller. The fluid reservoir has a bottom and is to hold a fluid. The differential pressure sensor is coupled to the bottom of the fluid reservoir and to sense a pressure difference between pressure exerted on the differential pressure sensor by the fluid and pressure exerted on the fluid in the fluid reservoir and to provide at least one signal that indicates a fluid level in the fluid reservoir. The controller is to receive the at least one signal and determine a fluid volume in the fluid reservoir based on the at least one signal. Also, the controller is to provide at least one of a fluid level signal that indicates the fluid level in the fluid reservoir and a fluid volume signal that indicates the fluid volume in the fluid reservoir.

19 Claims, 13 Drawing Sheets

(52) U.S. Cl.
CPC ........ *A61M 1/3666* (2013.01); *A61M 1/3693* (2013.01); *A61M 2205/3331* (2013.01); *A61M 2205/3334* (2013.01); *A61M 2205/3368* (2013.01); *A61M 2205/3389* (2013.01); *A61M 2205/3592* (2013.01); *A61M 2205/50* (2013.01); *A61M 2205/502* (2013.01); *A61M 2205/6018* (2013.01); *A61M 2205/6063* (2013.01)

(58) Field of Classification Search
CPC .. A61M 2205/3334; A61M 2205/3368; A61M 2205/3389; A61M 2205/3592; A61M 2205/50; A61M 2205/502; A61M 2205/6018; A61M 2205/6063
See application file for complete search history.

(56) References Cited

U.S. PATENT DOCUMENTS

| | | |
|---|---|---|
| 3,588,859 A | 6/1971 | Petree |
| 3,851,181 A | 11/1974 | Heule |
| 3,927,980 A | 12/1975 | Leonard |
| 4,006,745 A | 2/1977 | Sorenson et al. |
| 4,170,765 A | 10/1979 | Austin et al. |
| 4,177,649 A | 12/1979 | Venema |
| 4,193,004 A | 3/1980 | Lobdell et al. |
| 4,309,871 A | 1/1982 | Venema |
| 4,374,088 A | 2/1983 | Stenberg et al. |
| 4,464,164 A | 8/1984 | Troutner et al. |
| 4,466,804 A | 8/1984 | Hino |
| 4,490,331 A | 12/1984 | Steg, Jr. |
| 4,518,318 A | 5/1985 | Jensen et al. |
| 4,530,696 A * | 7/1985 | Bisera ............... A61M 5/16859 128/DIG. 13 |
| 4,599,093 A | 7/1986 | Steg, Jr. |
| 4,602,344 A | 7/1986 | Ferretti et al. |
| 4,642,089 A | 2/1987 | Zupkas et al. |
| 4,664,682 A | 5/1987 | Monzen |
| 4,678,404 A | 7/1987 | Lorett et al. |
| 4,701,101 A | 10/1987 | Sapoff |
| 4,705,497 A | 11/1987 | Shitaokoshi et al. |
| 4,782,451 A * | 11/1988 | Mazzarella ......... G01F 23/0069 340/680 |
| 4,828,543 A | 5/1989 | Weiss et al. |
| 4,846,800 A | 7/1989 | Ouriel et al. |
| 4,876,066 A | 10/1989 | Bringham et al. |
| 4,955,874 A | 9/1990 | Farrar et al. |
| 4,984,462 A | 1/1991 | Hass, Jr. et al. |
| 4,991,433 A | 2/1991 | Warnaka et al. |
| 5,039,430 A | 8/1991 | Corey, Jr. |
| 5,039,482 A | 8/1991 | Panzani et al. |
| 5,043,707 A | 8/1991 | Heinze |
| 5,049,146 A | 9/1991 | Bringham et al. |
| 5,055,198 A | 10/1991 | Shettigar |
| 5,060,512 A * | 10/1991 | Kanashige ............... G01F 23/18 340/614 |
| 5,061,236 A | 10/1991 | Sutherland et al. |
| 5,078,677 A | 1/1992 | Gentelia et al. |
| 5,110,549 A | 5/1992 | Gordon |
| 5,112,480 A | 5/1992 | Hukasawa |
| 5,120,303 A | 6/1992 | Hombrouckx |
| 5,135,485 A * | 8/1992 | Cohen ................. A61M 5/1684 324/606 |
| 5,147,187 A | 9/1992 | Ito et al. |
| 5,158,533 A | 10/1992 | Strauss et al. |
| 5,178,603 A | 1/1993 | Prince |
| 5,186,431 A | 2/1993 | Tamarim |
| 5,215,519 A | 6/1993 | Shettigar |
| 5,226,265 A | 7/1993 | Kelly |
| 5,240,380 A | 8/1993 | Mabe |
| 5,270,005 A | 12/1993 | Raible |
| 5,282,783 A | 2/1994 | Lindsay |
| 5,303,585 A | 4/1994 | Lichte |
| 5,304,164 A | 4/1994 | Lindsay |
| 5,318,510 A | 6/1994 | Cathcart |
| 5,399,074 A | 3/1995 | Nose et al. |
| 5,403,273 A | 4/1995 | Lindsay |
| 5,411,705 A | 5/1995 | Thor et al. |
| 5,458,566 A | 10/1995 | Herrig et al. |
| 5,458,567 A | 10/1995 | Cathcart |
| 5,458,579 A | 10/1995 | Chodorow et al. |
| 5,563,490 A | 10/1996 | Kawaguchi et al. |
| 5,563,584 A * | 10/1996 | Rader ................. A61M 5/1684 128/DIG. 13 |
| 5,586,085 A * | 12/1996 | Lichte ................. G01F 23/2962 367/165 |
| 5,591,399 A * | 1/1997 | Goldman ............ A61M 1/1698 128/DIG. 3 |
| 5,604,315 A * | 2/1997 | Briefer .................... G01F 23/18 73/718 |
| 5,619,993 A | 4/1997 | Lee |
| 5,667,485 A | 9/1997 | Lindsay |
| 5,725,357 A | 3/1998 | Nakazeki et al. |
| 5,756,940 A | 5/1998 | Van Driel et al. |
| 5,770,073 A | 6/1998 | Bach et al. |
| 5,775,879 A | 7/1998 | Durando |
| 5,800,721 A | 9/1998 | McBride |
| 5,823,045 A | 10/1998 | Van Driel et al. |
| 5,826,576 A | 10/1998 | West |
| 5,849,186 A | 12/1998 | Raneri et al. |
| 5,928,180 A | 7/1999 | Krivitski et al. |
| 5,955,672 A | 9/1999 | Van Driel et al. |
| 6,017,493 A | 1/2000 | Cambron et al. |
| 6,048,363 A | 4/2000 | Nagyszalanczy et al. |
| 6,123,519 A | 9/2000 | Kato et al. |
| 6,146,411 A * | 11/2000 | Noda .......................... A61F 7/12 607/105 |
| 6,164,325 A * | 12/2000 | Braun .................. B60K 15/061 123/509 |
| 6,287,270 B1 | 9/2001 | Fini |
| 6,337,049 B1 | 1/2002 | Tamari |
| 6,345,214 B1 | 2/2002 | Dulphy-Vigor et al. |
| 6,475,176 B2 | 11/2002 | Fini |
| 6,542,848 B1 * | 4/2003 | Neeser .................. F17C 13/025 700/281 |
| 6,562,012 B1 * | 5/2003 | Brown ................ A61M 5/1689 128/DIG. 13 |
| 6,564,627 B1 | 5/2003 | Sabini et al. |
| 6,592,340 B1 | 7/2003 | Horo et al. |
| 6,631,639 B1 * | 10/2003 | Dam .................... G01F 23/2961 340/621 |
| 6,652,495 B1 | 11/2003 | Walker |
| 6,694,570 B2 | 2/2004 | Chen |
| 6,770,048 B2 | 8/2004 | Fini |
| 6,931,926 B1 * | 8/2005 | Van Ee .................. F02D 33/003 73/291 |
| 7,072,769 B2 | 7/2006 | Fletcher-Haynes et al. |
| 7,147,614 B2 | 12/2006 | Fini |
| 7,591,812 B1 | 9/2009 | Tamari |
| 7,694,570 B1 * | 4/2010 | Dam ........................ G01F 1/662 310/328 |
| 7,982,612 B2 * | 7/2011 | Braun .................. A61M 5/1684 340/572.1 |
| 8,105,265 B2 | 1/2012 | Demers et al. |
| 8,394,321 B2 * | 3/2013 | Franzoni ................ A61M 1/342 422/44 |
| 8,409,124 B2 | 4/2013 | Steffens et al. |
| 8,500,673 B2 * | 8/2013 | Zanotti ................. A61M 1/3627 604/6.11 |
| 8,506,513 B2 | 8/2013 | Rossi et al. |
| 8,734,376 B2 | 5/2014 | Simpson et al. |
| 9,011,769 B2 | 4/2015 | Silvestri et al. |
| 2001/0013822 A1 | 8/2001 | Nazarian et al. |
| 2001/0050256 A1 | 12/2001 | Krivitski |
| 2002/0032399 A1 | 3/2002 | Fini |
| 2002/0033181 A1 | 3/2002 | Groth et al. |
| 2002/0038392 A1 * | 3/2002 | De La Huerga .. A61M 5/14212 710/8 |
| 2002/0085952 A1 | 7/2002 | Ellingboe et al. |
| 2002/0094300 A1 | 7/2002 | Yokoyama et al. |
| 2002/0133066 A1 | 9/2002 | Miller et al. |
| 2003/0033871 A1 | 2/2003 | Carroll et al. |

(56) References Cited

U.S. PATENT DOCUMENTS

| | | |
|---|---|---|
| 2003/0035730 A1 | 2/2003 | Schob |
| 2003/0045772 A1 | 3/2003 | Riech et al. |
| 2003/0139643 A1 | 7/2003 | Smith et al. |
| 2003/0144646 A1* | 7/2003 | Se .................. A61M 1/02 604/409 |
| 2003/0175151 A1 | 9/2003 | Ghelli et al. |
| 2004/0047737 A1 | 3/2004 | Nose et al. |
| 2004/0064292 A1 | 4/2004 | Beck et al. |
| 2004/0152944 A1 | 8/2004 | Medvedev et al. |
| 2005/0025630 A1 | 2/2005 | Ayre et al. |
| 2005/0119600 A1* | 6/2005 | Lucke .............. A61M 1/3627 604/6.15 |
| 2005/0230313 A1 | 10/2005 | O'Mahony et al. |
| 2006/0015056 A1* | 1/2006 | Ellingboe .......... A61M 1/3621 604/6.11 |
| 2006/0089695 A1 | 4/2006 | Bolea et al. |
| 2006/0092360 A1 | 5/2006 | Hong |
| 2006/0150596 A1 | 7/2006 | Takahashi et al. |
| 2006/0167400 A1 | 7/2006 | Ellingboe et al. |
| 2006/0226087 A1 | 10/2006 | Robinson et al. |
| 2006/0260392 A1* | 11/2006 | Hedrick .............. B64D 37/00 73/292 |
| 2006/0277269 A1 | 12/2006 | Dent et al. |
| 2007/0017518 A1 | 1/2007 | Farrugia et al. |
| 2007/0110612 A1 | 5/2007 | Ito |
| 2007/0142923 A1 | 6/2007 | Ayre et al. |
| 2007/0194981 A1 | 8/2007 | Hagg et al. |
| 2007/0209662 A1 | 9/2007 | Bowen et al. |
| 2008/0027368 A1 | 1/2008 | Kollar et al. |
| 2008/0078382 A1 | 4/2008 | LeMahieu et al. |
| 2008/0171960 A1 | 7/2008 | Brieske et al. |
| 2008/0245530 A1 | 10/2008 | Kuzmichev |
| 2008/0275377 A1 | 11/2008 | Paolini et al. |
| 2009/0012443 A1 | 1/2009 | Ghelli et al. |
| 2009/0099498 A1* | 4/2009 | Demers .............. A61M 1/106 604/6.09 |
| 2009/0149950 A1 | 6/2009 | Wampler |
| 2010/0042038 A1 | 2/2010 | Urdahl et al. |
| 2010/0140182 A1 | 6/2010 | Chapman et al. |
| 2010/0275953 A1 | 11/2010 | Orue Orue et al. |
| 2010/0280430 A1* | 11/2010 | Caleffi .............. A61M 1/342 604/5.01 |
| 2011/0098625 A1 | 4/2011 | Masala et al. |
| 2011/0257576 A1 | 10/2011 | Simpson et al. |
| 2011/0257578 A1 | 10/2011 | Zanotti et al. |
| 2011/0257579 A1* | 10/2011 | Rossi .................. A61M 1/3627 604/6.15 |
| 2012/0067133 A1* | 3/2012 | Waldrop ............ G01L 19/0015 73/753 |
| 2012/0130299 A1 | 5/2012 | Knott et al. |
| 2012/0226446 A1* | 9/2012 | Nelson ................ A61M 5/168 702/25 |
| 2013/0017119 A1 | 1/2013 | Silvestri et al. |
| 2013/0303965 A1 | 11/2013 | Rossi et al. |
| 2013/0331758 A1* | 12/2013 | Meibaum ............. A61M 1/30 604/5.04 |
| 2014/0278156 A1* | 9/2014 | Thompson ........ A61M 5/16831 702/55 |
| 2015/0100253 A1* | 4/2015 | Austerlitz .............. G01F 22/00 702/55 |
| 2015/0196703 A1 | 7/2015 | Silvestri et al. |
| 2015/0367120 A1* | 12/2015 | Kusters ................ A61M 39/08 137/15.09 |

FOREIGN PATENT DOCUMENTS

| | | |
|---|---|---|
| CN | 1197677 A | 11/1998 |
| CN | 1458851 A | 11/2003 |
| DE | 2455229 A1 | 5/1976 |
| DE | 2754894 A1 | 6/1979 |
| DE | 3935502 A1 | 5/1991 |
| DE | 19840399 A1 | 3/1999 |
| DE | 102004040441 A1 | 6/2006 |
| DE | 102005001779 A1 | 9/2006 |
| DE | 102005029682 A1 | 12/2006 |
| DE | 102007026010 A1 | 12/2008 |
| EP | 0371173 A1 | 6/1990 |
| EP | 0472480 B1 | 2/1992 |
| EP | 0587251 B1 | 3/1994 |
| EP | 0820775 B1 | 1/1998 |
| EP | 0952433 A1 | 10/1999 |
| EP | 1053760 A2 | 11/2000 |
| EP | 1070509 A2 | 1/2001 |
| EP | 0690730 B1 | 5/2002 |
| EP | 1210956 B1 | 6/2002 |
| EP | 0766974 B1 | 9/2006 |
| EP | 2754458 A2 | 7/2014 |
| EP | 2435106 B1 | 11/2014 |
| EP | 2842584 A1 | 3/2015 |
| FR | 2811752 A1 | 1/2002 |
| GB | 2009862 A | 6/1979 |
| GB | 2109934 A | 6/1983 |
| JP | S5623960 A | 3/1981 |
| JP | S57500411 A | 3/1982 |
| JP | S62258671 A | 11/1987 |
| JP | 03091352 U | 9/1991 |
| JP | H03091352 U | 8/1994 |
| JP | 819602 A | 1/1996 |
| JP | H08506982 A | 7/1996 |
| JP | 2944749 B2 | 6/1999 |
| JP | H11506701 A | 6/1999 |
| JP | 2000000299 A | 1/2000 |
| JP | 2001503665 A | 3/2001 |
| JP | 2001204815 A | 7/2001 |
| JP | 2001514939 A | 9/2001 |
| JP | 2001523339 A | 11/2001 |
| JP | 2002165878 A | 6/2002 |
| JP | 2002336348 A | 11/2002 |
| JP | 2003052717 A | 2/2003 |
| JP | 2003126246 A | 5/2003 |
| JP | 2005066013 A | 3/2005 |
| JP | 2006025531 A | 9/2006 |
| JP | 2006325750 A | 12/2006 |
| JP | 2007130290 A | 5/2007 |
| JP | 2008597 A | 1/2008 |
| JP | 2008194386 A | 8/2008 |
| JP | 2008270595 A | 11/2008 |
| JP | 2009240428 A | 10/2009 |
| JP | 2009287593 A | 12/2009 |
| JP | 2011076394 A | 4/2011 |
| WO | WO1994021311 A2 | 9/1994 |
| WO | WO1996024397 A2 | 8/1996 |
| WO | WO1997033672 A1 | 9/1997 |
| WO | WO1998020957 A1 | 5/1998 |
| WO | WO1998048868 A1 | 11/1998 |
| WO | WO1999008734 A1 | 2/1999 |
| WO | WO1999065413 A1 | 12/1999 |
| WO | WO2000015154 A1 | 3/2000 |
| WO | WO2000044415 A1 | 8/2000 |
| WO | WO2001047442 A1 | 7/2001 |
| WO | WO2001076656 A2 | 10/2001 |
| WO | WO2002039931 A1 | 5/2002 |
| WO | WO2002039933 A1 | 5/2002 |
| WO | WO2002095675 A1 | 11/2002 |
| WO | WO2003026724 A1 | 4/2003 |
| WO | WO2006021295 A1 | 2/2006 |
| WO | WO2006057650 A2 | 7/2006 |
| WO | 2006122282 A2 | 11/2006 |
| WO | 2007018513 A1 | 2/2007 |
| WO | WO2008119993 A1 | 10/2008 |
| WO | 2009144522 A1 | 12/2009 |
| WO | 2010041604 A1 | 4/2010 |

OTHER PUBLICATIONS

Definition of "Cylinder", downloaded from http://dictionary.reference.com/browse/cylinder, download on Apr. 28, 2014, 3 pages.

European Search Report issued in EP 10160436, dated Nov. 5, 2010, 9 pages.

European Search Report issued in EP Application No. 03004815, completed Apr. 25, 2003, 3 pages.

(56) References Cited

OTHER PUBLICATIONS

European Search Report issued in EP Application No. 11162020, dated Nov. 7, 2011, 8 pages.
European Search Report issued in EP Application No. 11173655, completed Nov. 30, 2011, 9 pages.
European Search Report issued in EP Application No. 12159592, dated Apr. 24, 2012, 6 pages.
Extended European Search Report issued in 14188440.3, dated Jan. 30, 2015, 7 pages.
Fischer, Gerhard, Betriebsmesstechnik, unveranderte Auflage, VEB Verlag Technik Berlin, 1986, 3 pages (machine translations: Business measuring technique, unchanged edition).
Henriksen Kerm et al., "Envisioning Patient Safety in the Year 2025: Eight Perspectives", Advances in Patient Safety: New Directions and Alternative Approaches, Agency for Healthcare Research and Quality, vol. 1, Aug. 2008.
International Preliminary Report on Patentability issued in PCT/EP2010/055444, dated Oct. 5, 2011, 10 pages (with English translation).
International Preliminary Report on Patentability issued in PCT/IB2014/061491 dated Dec. 1, 2016, 12 pages.
International Preliminary Report on Patentability, Chapter II, issued in PCT/EP2010/055522, (with translation) dated May 31, 2011, 13 pages.
International Search Report and Written Opinion issued in PCT/EP2010/055444, dated Aug. 20, 2010, 10 pages (English Translation of SR).
International Search Report and Written Opinion issued in PCT/EP2010/055522, (with translation) dated Aug. 6, 2010, 10 pages.
International Search Report and Written Opinion issued in PCT/IB2011/051639, dated Nov. 18, 2011, 15 pages.
International Search Report and Written Opinion issued in PCT/IB2014/061491, dated Mar. 6, 2015, 16 pages.
International Search Report issued in PCT/IB2012/053497, completed Nov. 15, 2012, 4 pages.
Klonoff, David C., "Designing an Artificial Pancreas System to be Compatible with Other Medical Devices", Journal of Diabetes Science and Technology, vol. 2, No. 5, Sep. 2008, pp. 741-745.
Terumo Europe Cardiovascular Systems, Innovative Products for the Treatment of Cardiovascular Disease, 2006 Terumo Europe, 105 pages.
Van der Togt, Remko et al., "Electromagnetic Interference From Radio Frequency Identification Inducing Potentially Hazardous Incidents in Critical Care medical Equipment", JAMA, Jun. 25, 2008, vol. 299, No. 24, 7 pages.
Weber, Tim, "Talking Barcodes that Change our Lives", BBC News, published April 48, 2004, 3 pages.
Wikipedia. "Fullstandmessung" [online]. Retrieved from https://de.wikipedia.org/w/index.php?title=F%C3%BCIIstandmessung&oldid=69998631, last modified Jan. 30, 2010. English translation retreived from https://en.wikipedia.org/wiki/Level_sensor, Oct. 18, 2016.

* cited by examiner

BLOOD RESERVOIR WITH FLUID VOLUME MEASUREMENT BASED ON PRESSURE SENSOR

CROSS-REFERENCE TO RELATED APPLICATION

This application is a national stage application of PCT/IB2014/061491, internationally filed May 16, 2014, which is herein incorporated by reference in its entirety.

TECHNICAL FIELD

The disclosure relates generally to perfusion and autotransfusion systems and more particularly to a blood reservoir having a pressure sensor.

BACKGROUND

Perfusion entails encouraging physiological solutions, such as blood, through vessels in the body or some portion of the body of a human or other animal. Perfusion can be employed in intracorporeal and extracorporeal circulation, such as during cardiopulmonary bypass surgery and other surgeries and during various therapeutic treatments. Perfusion is useful in maintaining the viability of body parts, such as specific organs or limbs, while the body part remains within the body or while the body part is exterior to the body, such as for transplantation or temporarily removal of a body part to provide access to other body structures. Perfusion can be used for a short period of time, such as less than about six hours, or for extended periods of time, such as greater than about six hours.

Sometimes, blood perfusion systems include one or more pumps in an extracorporeal circuit that is interconnected with the vascular system of a patient. Typically, cardiopulmonary bypass (CPB) surgery utilizes a perfusion system that allows for the temporary cessation of the heart by replacing the functions of the heart and lungs, which creates a still operating field and allows for the surgical correction of problems, such as vascular stenosis, valvular disorders, and congenital heart and great vessel defects. Perfusion systems for cardiopulmonary bypass surgery include an extracorporeal blood circuit that includes at least one pump and an oxygenation device to replace the functions of the heart and lungs.

In cardiopulmonary bypass procedures, oxygen-poor blood is gravity-drained or vacuum suctioned from a large vein entering the heart or from other veins (e.g., a femoral vein) in the body and transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is then returned through an arterial line to the aorta, femoral, or other main artery. Medical personnel configure the perfusion system prior to each bypass procedure, which can be a time consuming process that entails significant manual input of information related to components of the system.

SUMMARY

Example 1 is a system including a fluid reservoir, a differential pressure sensor, and a controller. The fluid reservoir has a bottom and is to hold a fluid. The differential pressure sensor is coupled to the bottom of the fluid reservoir and to sense a pressure difference between pressure exerted on the differential pressure sensor by the fluid and pressure exerted on the fluid in the fluid reservoir and to provide at least one signal that indicates a fluid level in the fluid reservoir. The controller is to receive the at least one signal and determine a fluid volume in the fluid reservoir based on the at least one signal. The controller is to provide at least one of a fluid level signal that indicates the fluid level in the fluid reservoir and a fluid volume signal that indicates the fluid volume in the fluid reservoir.

In Example 2, the system of Example 1 in which the differential pressure sensor has a first side to sense the pressure exerted on the differential pressure sensor by the fluid and a second side open to the atmosphere to sense atmospheric pressure.

In Example 3, the system of any of Examples 1 and 2 in which the differential pressure sensor has a first side to sense the pressure exerted on the differential pressure sensor by the fluid and a second side fluidically coupled to the top of the fluid reservoir to sense the pressure exerted on the fluid in the fluid reservoir.

In Example 4, the system of any of Examples 1-3 in which the differential pressure sensor includes a first sensor to sense the pressure exerted on the differential pressure sensor by the fluid and a second sensor to sense the pressure exerted on the fluid in the fluid reservoir.

In Example 5, the system of any of Examples 1-4 in which the at least one of the fluid level signal that indicates the fluid level in the fluid reservoir and the fluid volume signal that indicates the fluid volume in the fluid reservoir is received by a heart lung machine that adjusts an operating parameter of the heart lung machine based on the at least one of the fluid level signal that indicates the fluid level in the fluid reservoir and the fluid volume signal that indicates the fluid volume in the fluid reservoir.

In Example 6, the system of any of Examples 1-5 in which the at least one of the fluid level signal that indicates the fluid level in the fluid reservoir and the fluid volume signal that indicates the fluid volume in the fluid reservoir is received by a display system that displays at least one of the fluid level in the fluid reservoir and the fluid volume in the fluid reservoir.

In Example 7, the system of any of Examples 1-6 in which the differential pressure sensor is integrated into the bottom of the fluid reservoir.

In Example 8, the system of any of Examples 1-7 in which the differential pressure sensor is one of snap fit and adhesively attached to the bottom of the fluid reservoir.

In Example 9, the system of any of Examples 1-8 in which the differential pressure sensor is disposable.

In Example 10, the system of any of Examples 1-9 in which the controller is part of a heart lung machine.

In Example 11, the system of any of Examples 1-10 in which the controller is part of a display system.

In Example 12, the system of any of Examples 1-11 in which the controller is part of the differential sensor.

Example 13 is a sensor system including a first pressure sensor, a second pressure sensor, and a controller. The first pressure sensor is coupled to a fluid reservoir that holds a fluid and has a bottom. The first pressure sensor is coupled to the bottom of the fluid reservoir and is to provide a first signal that indicates hydrostatic pressure exerted by the fluid on the first pressure sensor. The second pressure sensor is to provide a second signal that indicates pressure exerted on the fluid in the fluid reservoir. The controller is to determine at least one of a fluid level in the fluid reservoir and a fluid volume in the fluid reservoir based on the first signal and the second signal.

In Example 14, the sensor system of Example 13 in which the second pressure sensor is open to the atmosphere to sense atmospheric pressure.

In Example 15, the sensor system of any of Examples 13 and 14 in which the second pressure sensor is coupled to the top of the fluid reservoir to sense the pressure exerted on the fluid in the fluid reservoir.

In Example 16, the sensor system of any of Examples 13-15 in which the first pressure sensor and the second pressure sensor are part of a differential pressure sensor.

Example 17 is a method including providing a fluid reservoir having a bottom and providing a differential pressure sensor coupled to the bottom of the fluid reservoir. The differential pressure sensor sensing a pressure difference between pressure exerted on the differential pressure sensor by fluid in the fluid reservoir and pressure exerted on the fluid in the fluid reservoir, and providing at least one signal that indicates a level of the fluid in the fluid reservoir. A controller receiving the at least one signal and determining a fluid volume in the fluid reservoir based on the at least one signal. The controller providing at least one of a fluid level signal that indicates the fluid level in the fluid reservoir and a fluid volume signal that indicates the fluid volume in the fluid reservoir.

In Example 18, the method of Example 17 in which sensing a pressure difference includes sensing the pressure exerted on the differential pressure sensor by the fluid on a first side of the differential pressure sensor and sensing atmospheric pressure on a second side of the differential sensor.

In Example 19, the method of any of Examples 17 and 18 in which sensing a pressure difference includes sensing the pressure exerted on the differential pressure sensor by the fluid on a first side of the differential pressure sensor and sensing through fluidic coupling to the top of the fluid reservoir the pressure exerted on the fluid in the fluid reservoir.

In Example 20, the method of any of Examples 17-19 in which sensing a pressure difference includes sensing the pressure exerted on the differential pressure sensor by the fluid via a first sensor and sensing the pressure exerted on the fluid in the fluid reservoir via a second sensor.

Embodiments shown and described herein can be described with reference to a blood level sensor system and/or a blood volume sensor system. As described herein, where the geometry of the blood reservoir is known, it is possible to provide either a fluid level or a fluid volume, as the volume of fluid in the reservoir can be calculated from the detected or sensed blood level and the known geometry of the reservoir.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
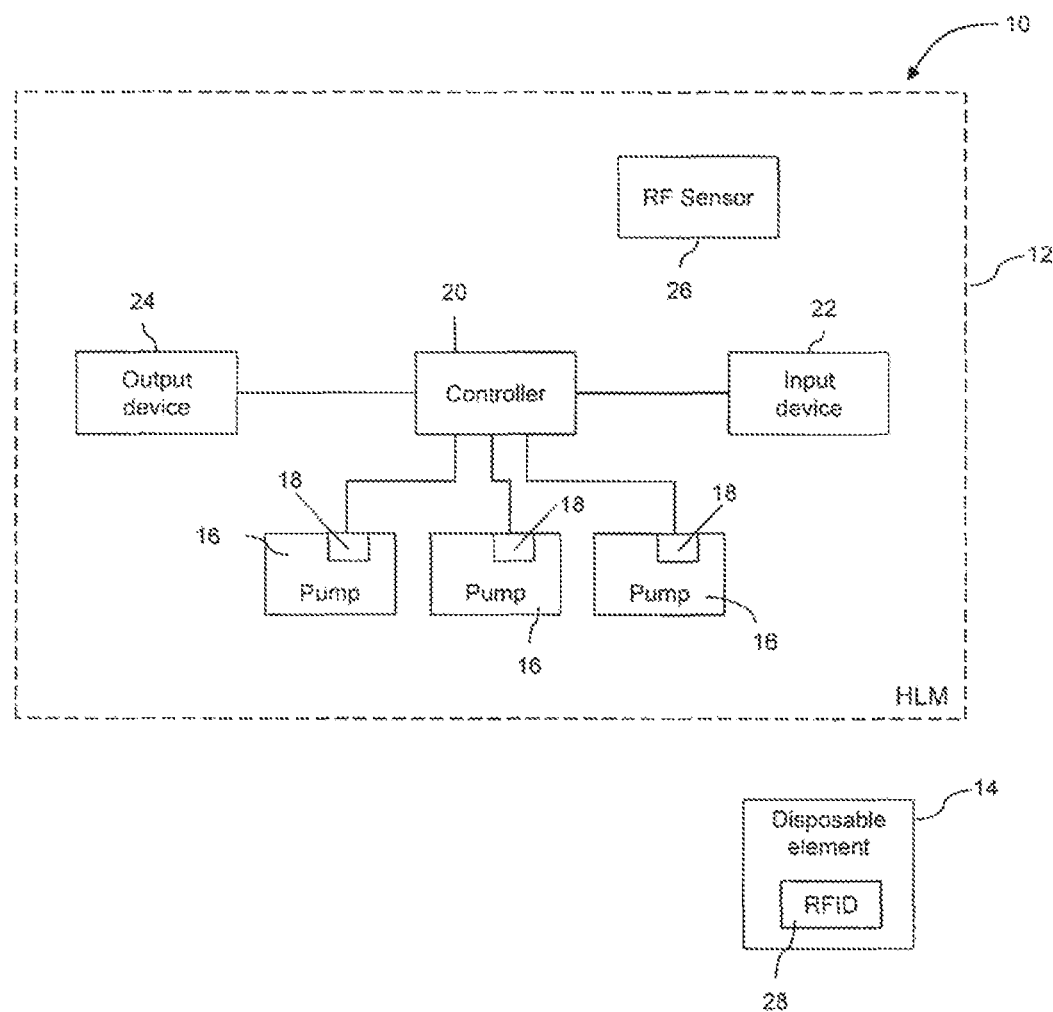
FIG. 1 is an illustration of an integrated perfusion system in accordance with embodiments described in the disclosure.

While the disclosure includes various modifications and alternative forms, embodiments have been shown by way of example in the drawings and are described below. The intention is not to limit the disclosure to the embodiments described. On the contrary, the intention is to cover all modifications, equivalents, and alternatives falling within the scope of the disclosure as defined by the appended claims.

DETAILED DESCRIPTION

The disclosure relates to a perfusion system that is easy to set-up, use, and monitor during a bypass procedure, and the disclosure relates to an autotransfusion system. In some embodiments, the disclosure relates to a sensor system that can be used to monitor a blood level or blood volume in a blood reservoir. In some embodiments, the sensor system can be utilized in an integrated perfusion system in which the components are configured to communicate with the perfusion system. In some embodiments, the sensor system can be utilized in a perfusion system lacking communication with components. In some embodiments, the sensor system can be utilized in an autotransfusion system. In some embodiments, the sensor system can be considered a blood level sensor system or a blood volume sensor system, where blood volume is ascertainable from blood level based on a known geometric configuration of the blood reservoir.

FIG. 1 is an illustration of an integrated perfusion system 10 including a heart lung machine (HLM) 12 and a disposable element 14. While a single disposable element 14 is shown, in some embodiments, a plurality of different disposable elements 14 can be utilized with the HLM 12. Also, one example of HLM components is shown in the HLM 12, in some embodiments, the HLM 12 can include other components and/or a different number of components.

The HLM 12 includes three pump modules 16. Each of the pump modules 16 can be used to provide fluid or gas for delivery to or removal from the heart chambers and/or a surgical field. In one example, one of the pump modules 16 draws blood from the heart, another provides surgical suction, and a third provides cardioplegia fluid (a high potassium solution to arrest the heart). Additional pump modules 16 (not shown) can be added to provide additional fluid transfer. In some embodiments, the HLM 12 includes as few as two pump modules 16 or as many as seven pump modules 16. In some embodiments, the pump modules 16 can be roller or peristaltic pumps. In some embodiments, one or more of the pump modules 16 can be a centrifugal pump.

Each pump module 16 includes a corresponding control unit 18. In some embodiments, each control unit 18 is configured to operate and monitor the operation of the corresponding pump module 16. In some embodiments, each control unit 18 includes one or more input devices (not illustrated), such as switches, knobs, buttons, and touch screens, so the perfusionist can adjust the operation of the pump module 16. In some embodiments, each pump module 16 includes an alphanumeric display that the control unit 18 uses to display, for example, the value of a setting, the value of a current operating parameter, and/or confirmation that the pump module 16 is operating normally.

The HLM 12 includes a controller 20 in communication with the control units 18 and configured to operate the HLM 12. In some embodiments, the controller 20 is configured to monitor one or more sensors in the HLM 12 and/or in the disposable element 14 to monitor operation of the HLM 12. Examples of sensors include flow meters, pressure sensors, temperature sensors, and blood gas analyzers.

While the control units 18 and the controller 20 are illustrated as distinct elements, in some embodiments, these elements can be combined in a single controller. In some embodiments, one or more of the control units 18, in combination, can be configured to operate the HLM 12, thereby negating a need for the controller 20.

The controller 20 communicates with an input device 22 and an output device 24. The input device 22 can be used by the perfusionist to enter information that is not otherwise entered into the control units 18. The output device 24 can be used by the HLM 12 to display pertinent information to the perfusionist. In some embodiments, the input device 22 can be a key pad, a keyboard, and/or a touch screen. In some embodiments, the output device 24 can be a monitor. In some embodiments, the input device 22 and/or the output device 24 can be a computer, such as a personal computer, a laptop computer, a notebook computer, or a tablet computer. In some embodiments, the input device 22 and the output device 24 can be in a single computer.

The HLM 12 includes an RF sensor 26. In some embodiments, the RF sensor 26 can be configured to receive information from an active RFID tag placed on the disposable element 14. In some embodiments, the RF sensor 26 can be a hand held device that is used to scan a passive RFID tag on the disposable element 14. In some embodiments, the RF sensor 26 can be replaced with any suitable wireless communication receiver.

The disposable element 14 includes an RFID tag 28. In some embodiments, the disposable element 14 includes an active RFID tag and/or a passive RFID tag configured to communicate with the RF sensor 26. In some embodiments, the RFID tag 28 can be replaced with any suitable wireless communication transmitter. In some embodiments, the system includes one or more of the RFID configurations disclosed in U.S. patent application Ser. No. 12/763,561, filed on Apr. 20, 2010, which is hereby incorporated by reference in its entirety.

Passive RFID tags lack a power supply and, in some embodiments, are powered by an induced current caused by an incoming radio-frequency scan. Since passive RFID tags lack a power supply, they are smaller and less expensive than active RFID tags. Active RFID tags include an onboard power supply, such as a battery. While this increases the size and expense of the RFID tag, the active RFID tag can store more information and transmit further. RFID tags, whether active or passive, can be selected to transmit at a variety of frequencies depending on need. Options include low frequency (about 100 to 500 kilohertz), high frequency (about 10 to 15 megahertz), ultra high frequency (about 860 to 960 megahertz), and microwave frequency (about 2.45 gigahertz) RFID tags.

The disposable element 14 can be one, two, or a plurality of different disposable elements that can be used in conjunction with the HLM 12. Examples of disposable elements 14 include tubing sets, blood reservoirs, oxygenators, heat exchangers, and arterial filters. In some embodiments, a tubing set includes a number of different tubes, potentially of different lengths and/or sizes, for providing fluid flow between components of the HLM 12 as well as providing fluid flow between the HLM 12 and a patient.

In some embodiments, the disposable element 14 can be a blood reservoir such as a venous blood reservoir, a vent blood reservoir, or a cardiotomy or suction blood reservoir. In some embodiments, the disposable element 14 can be a blood reservoir that combines one or more of a venous blood reservoir, a vent reservoir, and a suction reservoir in a single structure. In some embodiments, one or more of the aforementioned sensors can be disposable elements that include an RFID tag 28 to provide information identifying the sensor and/or for transmitting sensed values to the controller 20.

The RFID tag 28 can be attached to the disposable element 14 and programmed with or otherwise configured to include a variety of information pertaining to the disposable element 14. In some embodiments, the RFID tag 28 can be adhesively secured to the disposable element 14. In some embodiments, the RFID tag 28 can be molded into the disposable element 14. In some embodiments the RFID tag 28 can be a standalone card, similar in size and shape to a credit card, which can be packed with the disposable element 14 in such a way that it can be removed by the user and swiped by the RF sensor 26.

In some embodiments, the RFID tag 28 can include data or identifying information for the disposable element 14, such as the name of the particular disposable element 14, a reference code, a serial number, a lot number, and/or an expiration date. In some embodiments, this information may be communicated to the controller 20 and used to confirm that the proper disposable elements 14 are being used for a particular setting or patient. For example, the controller 20 may recognize that a pediatric tubing set is being used in combination with an adult-sized blood reservoir or the controller 20 may recognize that an expected component is missing. The controller 20 can recognize potential mismatches in equipment as a result of the information provided by the RFID tag 28 attached to each of the one or more disposable elements 14.

In some embodiments, the RFID tag 28 can include descriptive or design information for the disposable element 14, such as materials, a list of components, priming volume of a component or tubing circuit, tubing size, tubing length, minimum and maximum working pressures, minimum and maximum working volume, and blood reservoir sizing information, such as blood reservoir dimensions. In some embodiments, this information can be communicated to the controller 20 and used by the controller 20 to at least partially configure and/or operate the HLM 12. For example, the controller 20 can use the sizing information provided from each of the disposable elements 14 to determine a working blood volume for the HLM 12.

In some embodiments, information obtained from the RFID tag 28 can be provided to the perfusionist. In some embodiments, the output device 24 can be configured to provide alphanumeric or graphical representations of the obtained information. In some embodiments, the RFID tag 28 can include instructional information displayed by the output device 24 to instruct the perfusionist in optimal setup and/or operation of a disposable element 14. In some embodiments, the output device 24 can be a computer such as a personal computer, a laptop computer, a notebook computer, or a tablet computer. In some embodiments, the RFID tag 28 can include displayable information that, for example, suggests an optimal circuit design based upon the components being used or provides updated use instructions. In some embodiments, information from the RFID tag 28 is displayed on an integrated data management system (DMS).

In some embodiments, the RFID tag 28 can include information provided by a manufacturer of the disposable element 14, such as technical features of the disposable element 14 that have changed from a previous version or batch and/or information that can be displayed by the output device 24 that requires the user to acknowledge receipt of the information before the controller 20 proceeds with a procedure. In some embodiments, the RFID tag 28 can receive error messages from the controller 20 and the RFID tag 28 can be returned to the manufacturer, thereby providing the manufacturer with feedback regarding the performance of the disposable element 14 as well as other components.

Figure 2:
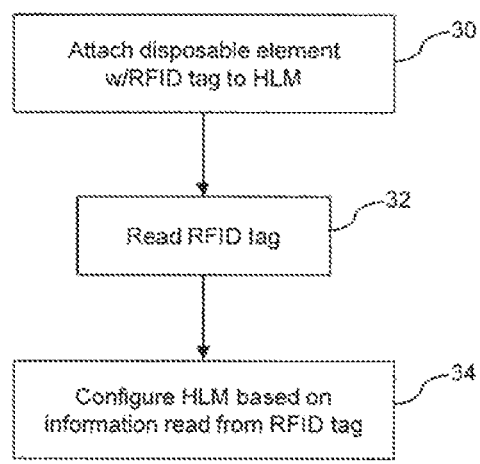
FIG. 2 is a flow diagram illustrating a method that can be carried out by the integrated perfusion system of FIG. 1.

FIG. 2 is a flow diagram illustrating a method that can be carried out using the perfusion system 10 of FIG. 1. At 30, a disposable element 14 having an RFID tag 28 is attached to the HLM 12. At 32, the RFID tag 28 is read, where the RFID tag 28 can be an active RFID tag or a passive RFID tag. At 34, the HLM 12 is configured based at least in part upon information that was read from the RFID tag 28. In some embodiments, the controller 20 automatically configures the HLM 12 in response to the information. In some embodiments, the RFID tag 28 can be read before the disposable element 14 is attached to the HLM 12. In some embodiments, the RFID tag 28 can be read after the disposable element 14 is attached to the HLM 12.

Figure 3:
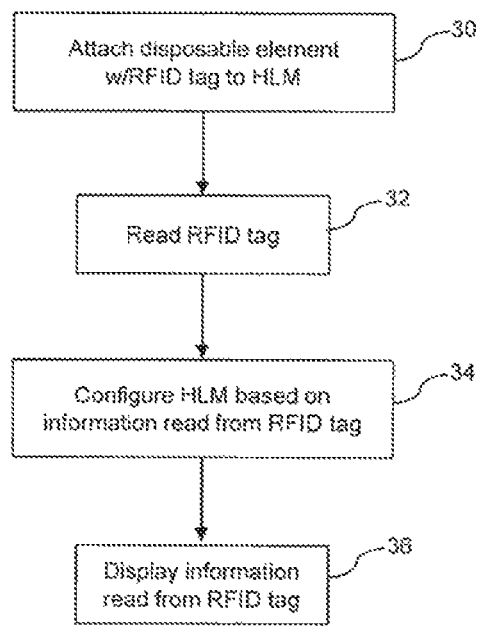
FIG. 3 is a flow diagram illustrating a method that can be carried out by the integrated perfusion system of FIG. 1.

FIG. 3 is a flow diagram illustrating a method that can be carried out using the perfusion system 10 of FIG. 1. The method of FIG. 3 is the same as the method of FIG. 2, with the addition that, at 36, at least some of the information read from the RFID tag 28 can be displayed on the output device 24.

Figure 4:
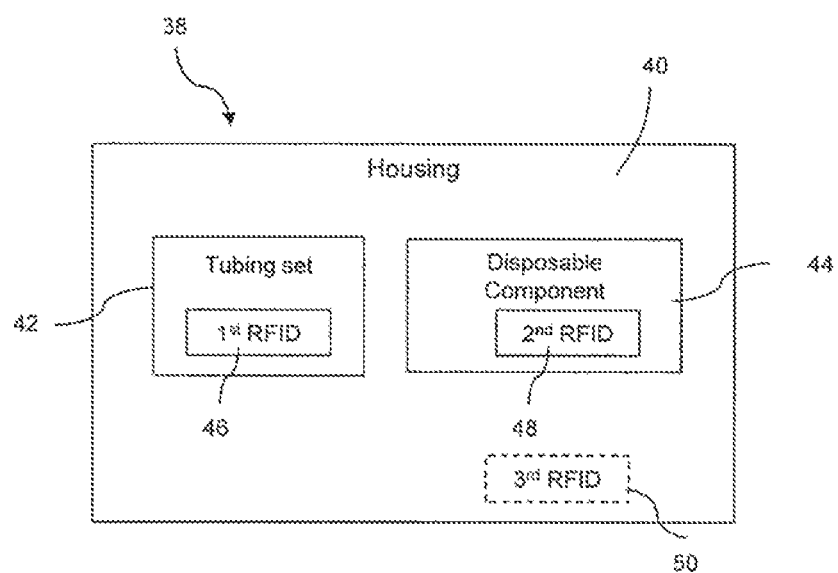
FIG. 4 is an illustration of a heart lung machine pack that can be utilized with the integrated perfusion system of FIG. 1.

FIG. 4 is an illustration of a heart lung machine pack 38 that can be utilized with the perfusion system 10 of FIG. 1. In some embodiments, the heart lung machine pack 38 can include all of the disposable elements 14 that will be used together for a patient and can be customized for the patient. In some embodiments, the heart lung machine pack 38 can include a housing 40 that, once filled, can be sealed to keep the contents clean and sterile.

The heart lung machine pack 38 includes a tubing set 42 and a disposable component 44. The tubing set 42 can include a plurality of different tubes. The disposable component 44 can be any of the disposable components discussed above with respect to the disposable element 14. In some embodiments, the heart lung machine pack 38 will include a plurality of different disposable components 44.

The tubing set 42 includes a first RFID tag 46 while the disposable component 44 includes a second RFID tag 48. As described above, each of the first RFID tag 46 and the second RFID tag 48 can be either an active or a passive RFID tag and include readable information pertaining to the component to which it is attached. In some embodiments, the housing 40 can include a third RFID tag 50 that, for example, identifies the contents of the heart lung machine pack 38. In some embodiments, the first RFID tag 46 and the second RFID tag 48 will not be included and the third RFID tag 50 can be encoded with all of the information for the tubing set 42 and the disposable component 44.

Figure 5A:
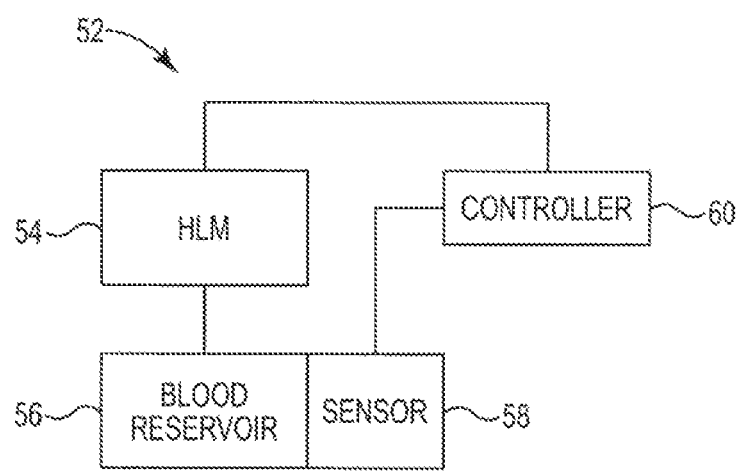
FIG. 5A is an illustration of a perfusion system in accordance with embodiments described in the disclosure.

FIG. 5A is an illustration of a perfusion system 52. In some embodiments, the perfusion system 52 can be similar to the perfusion system 10 of FIG. 1.

The perfusion system 52 includes an HLM 54, a blood reservoir 56, a fluid sensor 58, and a controller 60. In some embodiments, the HLM 54 can be similar to the HLM 12 (shown in FIG. 1). In some embodiments, the blood reservoir 56 can be a venous blood reservoir, a vent blood reservoir, or a cardiotomy or suction blood reservoir. In some embodiments, the blood reservoir 56 can be a blood reservoir that combines one or more of a venous blood reservoir, a vent reservoir, and/or a suction reservoir in a single structure.

The fluid sensor 58 can be configured to continuously monitor a variable blood level in the blood reservoir 56. The fluid sensor 58 provides one or more electrical signals that are proportional to the blood level in the blood reservoir 56. In some embodiments, as will be subsequently described, the fluid sensor 58 can be one or more pressure sensors for detecting the blood level in the blood reservoir 56. In some embodiments, the fluid sensor 58 can be one or more pressure sensors that provide voltage signals that correlate to pressure signals for detecting the blood level in the blood reservoir 56. In some embodiments, the fluid sensor 58 can be a differential pressure sensor that senses the difference between the hydrostatic pressure exerted on one side of the differential pressure sensor by the fluid in the blood reservoir and the pressure exerted on the fluid in the blood reservoir at, for example, the top of the blood reservoir and above the fluid. In some embodiments, the fluid sensor 58 can be two pressure sensors, where a first pressure sensor senses the hydrostatic pressure exerted on the first pressure sensor by the fluid in the blood reservoir and a second pressure sensor senses the pressure exerted on the fluid in the blood reservoir at, for example, the top of the blood reservoir and above the fluid.

The controller 60 can receive the one or more electrical signals from the fluid sensor 58 and determine or calculate the blood level and/or the blood volume in the blood reservoir 56. The controller 60 can determine or calculate the blood volume in the blood reservoir based on the one or more electrical signals as well as a known shape or geometry of the blood reservoir 56. In some embodiments, the blood reservoir 56 can include an RFID tag (not illustrated) that provides the controller 60 with information pertaining to the known geometry of the blood reservoir 56. In some embodiments, the volume of the blood reservoir is calculated according to one or more of the techniques described in U.S. patent application Ser. No. 12/763,561, filed on Apr. 20, 2010, previously incorporated by reference herein. In some embodiments, the volume of the blood reservoir 56 is calculated by integrating the level of blood in the reservoir against the known cross-sectional area of the blood reservoir 56 at various heights throughout the blood reservoir 56.

If the blood reservoir 56 is a hard shell blood reservoir, the known geometry of the blood reservoir 56 can include the cross-sectional area of the blood reservoir 56, or a width and depth of the blood reservoir 56 as well as details on how the cross-sectional area varies relative to height within the blood reservoir 56. If the blood reservoir 56 is a soft shell reservoir, the known geometry can be based at least in part upon a known lateral expansion rate of the soft shell reservoir relative to the blood level within the blood reservoir 56.

Figure 5B:
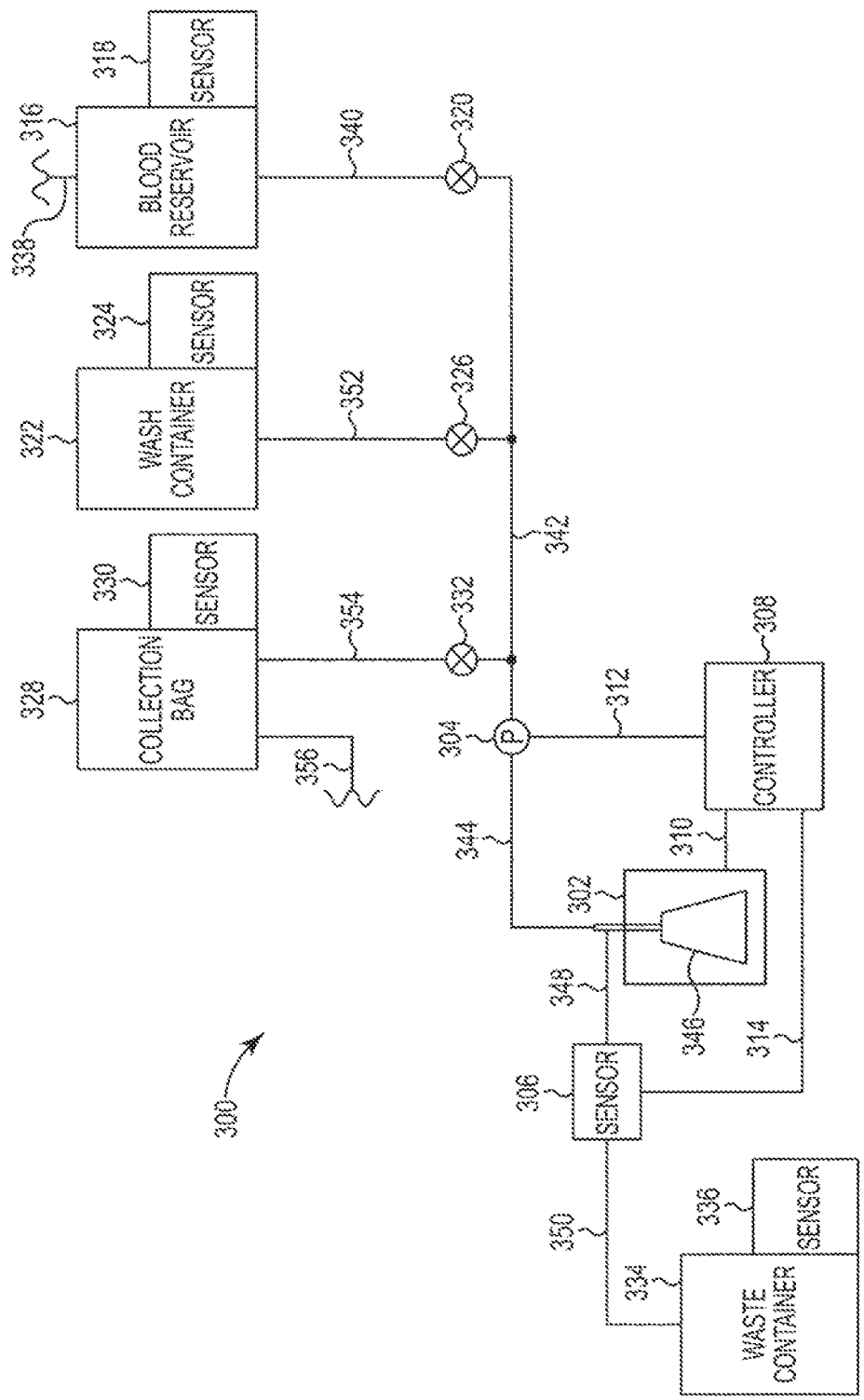
FIG. 5B is an illustration of an autotransfusion system in accordance with embodiments described in the disclosure.

FIG. 5B is an illustration of an autotransfusion system 300, according to some embodiments described in the disclosure. The autotransfusion system 300 includes a centrifuge 302, a pump 304, a sensor 306, and a controller 308. The controller 308 is operatively connected to the centrifuge 302, the pump 304, and the sensor 306 to provide the autotransfusion system 300. The controller 308 is communicatively coupled to the centrifuge 302 through a first communications path 310, to the pump 304 through a second communications path 312, and to the sensor 306 through a third communications path 314.

The autotransfusion system 300 further includes: a salvaged blood reservoir 316, a salvaged blood fluid sensor 318, and a salvaged blood valve 320; a wash solution container 322, a wash solution fluid sensor 324, and a wash solution valve 326; a collection bag 328, a collection fluid sensor 330, and a collection valve 332; and a waste container 334 and a waste fluid sensor 336. In some embodiments, the autotransfusion system 300 includes at least one but not all of the fluid sensors 318, 324, 330, and 336.

The controller 308 is operatively connected to each of the salvaged blood fluid sensor 318, the salvaged blood valve 320, the wash solution fluid sensor 324, the wash solution valve 326, the collection fluid sensor 330, the collection valve 332, and the waste fluid sensor 336. In some embodiments, the controller 308 is communicatively coupled (not shown for clarity) to each of the salvaged blood fluid sensor 318, the salvaged blood valve 320, the wash solution fluid sensor 324, the wash solution valve 326, the collection fluid sensor 330, the collection valve 332, and the waste fluid sensor 336.

In the autotransfusion system 300, an inlet line 338 suctions salvaged blood from an operation field of a patient or from another blood source and carries the suctioned blood to the salvaged blood reservoir 316. In a fill phase, the salvaged blood in the salvaged blood reservoir 316 is pumped through a salvaged blood line 340 and the salvaged blood valve 320 into a system line 342 by the pump 304. The salvaged blood is further pumped through a bowl inlet line 344 into a centrifuge bowl 346 in the centrifuge 302 by the pump 304. As the salvaged blood is pumped into the centrifuge bowl 346, the salvaged blood valve 320 is open and the other valves, including the wash solution valve 326 and the collection valve 332, are closed. In some embodiments, the centrifuge bowl 346 receives the shed or salvaged blood directly from the operation field or directly from the other source.

In the fill phase, the centrifuge bowl 346 is filled with the salvaged blood as the centrifuge 302 rotates or spins the centrifuge bowl 346. The spinning centrifuge bowl 346 separates the blood into components according to the relative densities of the components. The red blood cells, which are the densest components of the blood, are propelled outward, against the circumferential wall of the centrifuge bowl 346. Other components, such as white blood cells and platelets, are arranged in a thin layer, referred to as the buffy coat, directly adjacent the concentrated mass of red blood cells. A plasma layer that includes undesirable components is situated above the buffy coat. As filling the centrifuge bowl 346 continues, more of the red blood cells are pushed upward along the circumferential wall of the centrifuge bowl 346, which pushes the plasma layer out of an outlet at the top of the centrifuge bowl 346. The plasma flows through a first waste line 348 connected to the outlet of the centrifuge bowl 346, past the sensor 306, and through a second waste line 350 into the waste container 334. The sensor 306 senses when the buffy coat begins to come out of the outlet or when the buffy coat is at or near the top of the centrifuge bowl 346 and the sensor 306 provides a corresponding signal to the controller 308. In response to the signal from the sensor 306, the controller 308 stops the fill phase.

After the fill phase, the autotransfusion system 300 washes the blood in the centrifuge bowl 346 in a wash phase. Wash solution contained in the wash solution container 322 is pumped into the centrifuge bowl 346 by the pump 304. The wash solution is pumped through a wash solution line 352 and the wash solution valve 326 into the system line 342 by the pump 304. The wash solution is further pumped through the bowl inlet line 344 and into the centrifuge bowl 346 by the pump 304. As the wash solution is pumped into the centrifuge bowl 346, the wash solution valve 326 is open and the other valves, including the salvaged blood valve 320 and the collection valve 332, are closed. In some embodiments, the wash solution is a saline solution.

In the wash phase, the controller 308 controls the centrifuge bowl 346 and the pump 304 to wash the blood in the centrifuge bowl 346. In the wash phase, more of the plasma or supernatant that includes the undesirable components is removed and flows through the first waste line 348 connected to the outlet of the centrifuge bowl 346, past the sensor 306, and through the second waste line 350 and into the waste container 334.

After washing the concentrated red blood cells in the centrifuge bowl 346, the final product is pumped out of the centrifuge bowl 346 through the bowl inlet line 344 and into the system line 342 by the pump 304. The final product is further pumped through the collection valve 332 and the collection line 354 into the collection bag 328. In this emptying phase, the controller 308 opens the collection valve 332 and closes the other valves, including the salvaged blood valve 320 and the wash solution valve 326.

The final product of concentrated red blood cells in the collection bag 328 can be used for reinfusion back into the patient via outlet line 356.

Each of the fluid sensors 318, 324, 330, and 336 can be configured to continuously monitor a variable fluid level in its corresponding container or bag 316, 322, 328, and 334. Each of the fluid sensors 318, 324, 330, and 336 provides one or more electrical signals that are proportional to the fluid level in its corresponding container or bag 316, 322, 328, and 334. In some embodiments, as will be subsequently described, each of the fluid sensors 318, 324, 330, and 336 can be one or more pressure sensors for detecting the fluid level in its corresponding container or bag 316, 322, 328, and 334. In some embodiments, each of the fluid sensors 318, 324, 330, and 336 can be one or more pressure sensors that provide voltage signals that correlate to pressure signals for detecting the fluid level in its corresponding container or bag 316, 322, 328, and 334. In some embodiments, each of the fluid sensors 318, 324, 330, and 336 can be a differential pressure sensor that senses the difference between the hydrostatic pressure exerted on one side of the differential pressure sensor by the fluid in its corresponding container or bag 316, 322, 328, and 334 and the pressure exerted on the fluid at, for example, the top of its corresponding container or bag 316, 322, 328, and 334 and above the fluid. In some embodiments, each of the fluid sensors 318, 324, 330, and 336 can be two pressure sensors, where a first pressure sensor senses the hydrostatic pressure exerted on the first pressure sensor by the fluid in its corresponding container or bag 316, 322, 328, and 334 and a second pressure sensor senses the pressure exerted on the fluid at, for example, the top of its corresponding container or bag 316, 322, 328, and 334 and above the fluid.

The controller 308 can receive the one or more electrical signals from each of the fluid sensors 318, 324, 330, and 336 and determine or calculate the fluid level and/or the fluid volume in its corresponding container or bag 316, 322, 328, and 334. The controller 308 can determine or calculate the fluid volume based on the one or more electrical signals as well as a known shape or geometry of the corresponding container or bag 316, 322, 328, and 334. In some embodiments, one or more of the containers or bags 316, 322, 328, and 334 includes an RFID tag (not illustrated) that provides the controller 308 with information pertaining to the known geometry of the container or bag. In some embodiments, the volume of the container or bag 316, 322, 328, and 334 is calculated according to one or more of the techniques described in U.S. patent application Ser. No. 12/763,561, filed on Apr. 20, 2010, previously incorporated by reference herein. In some embodiments, the volume of the container or bag 316, 322, 328, and 334 is calculated by integrating the level of fluid against the known cross-sectional area of the container or bag 316, 322, 328, and 334 at various heights throughout the container or bag 316, 322, 328, and 334.

If the container or bag 316, 322, 328, and 334 is a hard shell reservoir, the known geometry can include the cross-sectional area of the container or bag 316, 322, 328, and 334, or a width and depth of the container or bag 316, 322, 328, and 334 as well as details on how the cross-sectional area varies relative to height within the container or bag 316, 322, 328, and 334. If the container or bag 316, 322, 328, and 334 is a soft shell reservoir, the known geometry can be based at least in part upon a known lateral expansion rate of the soft shell reservoir relative to the fluid level within the container or bag 316, 322, 328, and 334.

The auto transfusion system 300 can include one or more of the blood reservoir systems 70, 110, 150, and 190, described herein, to take the place of one or more of the fluid sensors 318, 324, 330, and 336 and the corresponding containers or bags 316, 322, 328, and 334. As used herein, the term blood reservoir can include one or more of the salvaged blood reservoir 316, the wash solution container 322, the collection bag 328, and the waste container 334. Also, as used herein, the term fluid reservoir can include one or more of the blood reservoirs 72, 112, 156, and 196 in the blood reservoir systems 70, 110, 150, and 190 and the salvaged blood reservoir 316, the wash solution container 322, the collection bag 328, and the waste container 334.

Figure 6:
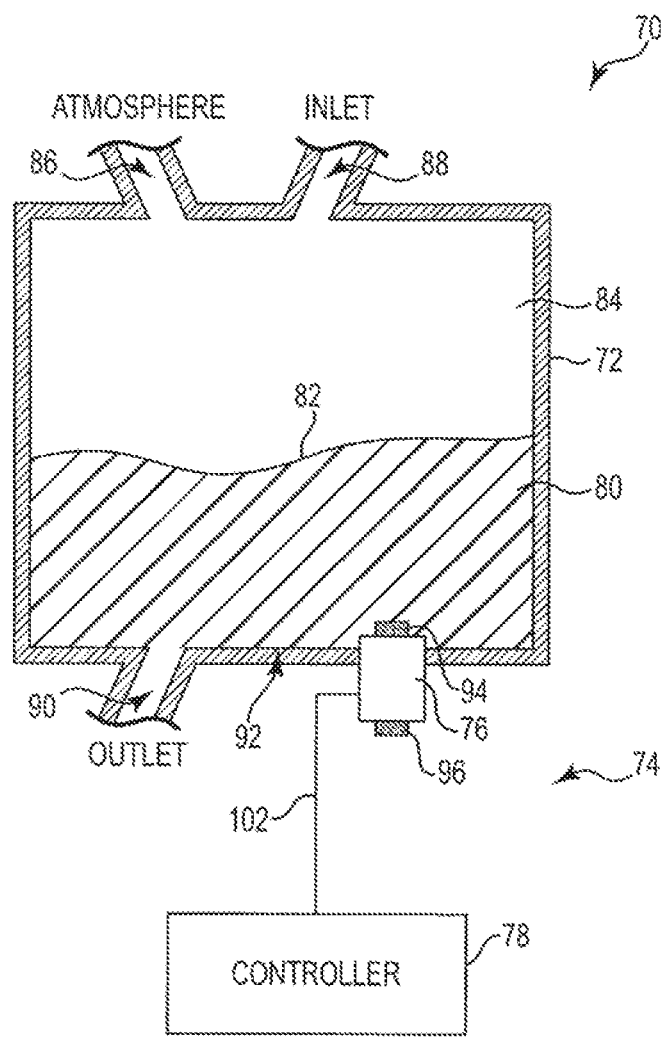
FIG. 6 is an illustration of a blood reservoir system that includes a differential pressure sensor and a hard shell blood reservoir "open" to the atmosphere.
Figure 7:
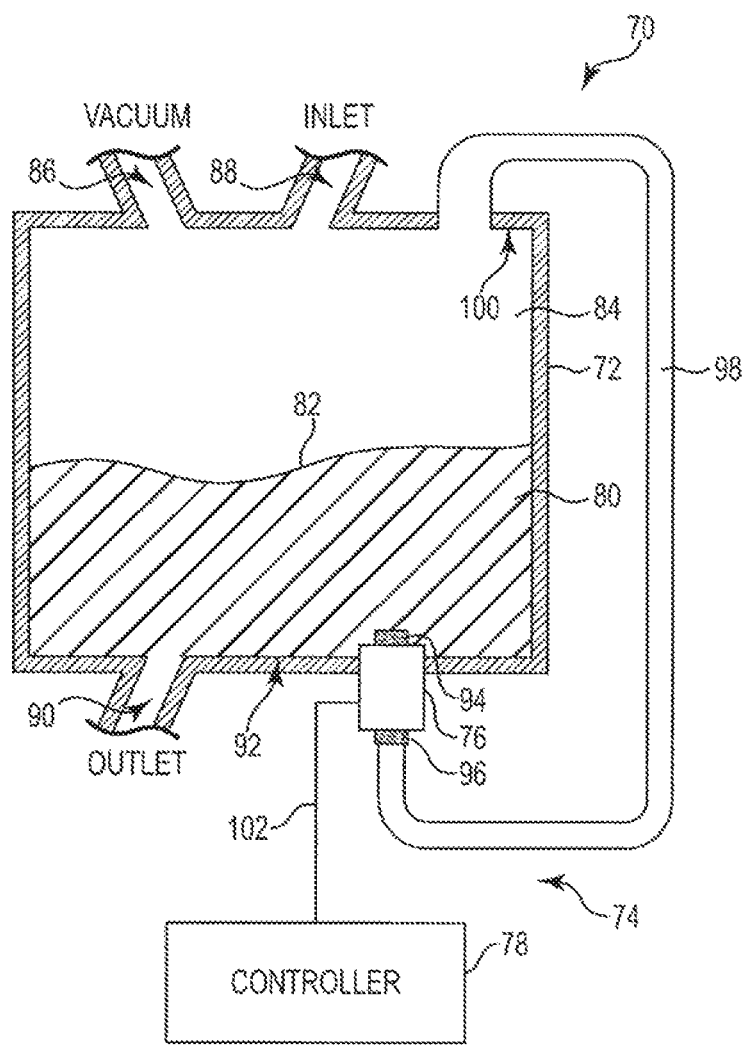
FIG. 7 is an illustration of a blood reservoir system that includes the differential pressure sensor and the hard shell blood reservoir "closed" and coupled to a vacuum.

FIGS. 6 and 7 are illustrations of a blood reservoir system 70 that can be used in a perfusion system, such as the perfusion system 10 of FIG. 1 and the perfusion system 52 of FIG. 5A. The blood reservoir system 70 can also be used in an autotransfusion system, such as autotransfusion system 300 of FIG. 5B. The blood reservoir system 70 includes a blood reservoir 72 and a sensor system 74 that includes a differential pressure sensor 76 and a controller 78. In some embodiments, the blood reservoir 72 can be similar to the blood reservoir 56. In some embodiments, the differential pressure sensor 76 can be similar to the fluid sensor 58. In some embodiments, the controller 78 can be similar to the controller 60.

FIG. 6 is an illustration of the blood reservoir system 70 with the blood reservoir 72 "open" to the atmosphere, such as when draining a patient by gravity. FIG. 7 is an illustration of the blood reservoir system 70 with the blood reservoir 72 "closed" and fluidically coupled to a vacuum, such as when draining a patient with vacuum.

The blood reservoir 72 is a rigid, hard shell blood reservoir. The blood reservoir 72 is illustrated containing a volume of fluid 80, such as blood, that defines an interface 82 between the volume of fluid 80 and the air or other gas 84 in the space above the volume of fluid 80 in the blood reservoir 72. The blood reservoir 72 can include a first opening 86 that can be left open to the atmosphere, as shown in FIG. 6, or fluidically coupled to a vacuum, as shown in FIG. 7, a second opening 88 that can be an inlet for the fluid, and a third opening 90 that can be an outlet for the fluid. In some embodiments, the blood reservoir 72 can be a rigid, hard shell blood reservoir with a known geometry that can include the cross-sectional area of the blood reservoir 72, or a width and depth of the blood reservoir 72, as well as details on how the cross-sectional area varies relative to height within the blood reservoir 72.

The differential pressure sensor 76 can be located at the bottom 92 of the blood reservoir 72 to sense the pressure difference between the pressure exerted on the differential pressure sensor 76 by the fluid in the blood reservoir 72 and the pressure exerted on the volume of fluid 80 from the air or other gas 84 above the volume of fluid 80 in the blood reservoir 72. The differential pressure sensor 76 provides a signal that indicates the fluid level in the blood reservoir 72 and the controller 78 determines or calculates the fluid volume based on the fluid level and the known geometric configuration of the blood reservoir 72.

To sense the pressure difference, a first side 94 of the differential pressure sensor 76 can be in contact with the volume of fluid 80 in the blood reservoir 72 to sense the hydrostatic pressure exerted on the first side 94 of the differential pressure sensor 76 by the volume of fluid 80. As shown in FIG. 6, a second side 96 of the differential pressure sensor 76 can be left open to the atmosphere to sense the atmospheric pressure, which is the pressure exerted on the volume of fluid 80 from above the volume of fluid 80 in the blood reservoir 72 with the first opening 86 left open to the atmosphere. Alternatively, as shown in FIG. 7, the second side 96 of the differential pressure sensor 76 can be fluidically coupled with a tube 98 to the top 100 of the blood reservoir 72, such that the second side 96 of the differential pressure sensor 76 is fluidically coupled to the air or other gas 84 above the volume of fluid 80 in the blood reservoir 72, to sense the pressure exerted on the volume of fluid 80 from above the volume of fluid 80 in the blood reservoir 72.

The differential pressure sensor 76 can provide at least one electrical signal that correlates to the pressure difference and the pressures exerted on the first and second sides 94 and 96 of the differential pressure sensor 76, where the at least one electrical signal indicates the fluid level in the blood reservoir 72. In some embodiments, the differential pressure sensor 76 can provide at least one voltage signal that indicates the fluid level in the blood reservoir 72. In some embodiments, the differential pressure sensor 76 can provide the at least one electrical signal as a wired electrical signal(s). In some embodiments, the differential pressure sensor 76 can provide the at least one electrical signal as a wireless signal(s).

The differential pressure sensor 76 can be integrated into the blood reservoir 72. In some embodiments, the differential pressure sensor 76 can be snap fit into the bottom of the blood reservoir 72. In some embodiments, the differential pressure sensor 76 can be adhesively attached to the bottom of the blood reservoir 72. In some embodiments, the differential pressure sensor 76 can be molded into the blood reservoir 72, such that the differential pressure sensor 76 can be at least partially protected by the plastic material of the blood reservoir 72.

In some embodiments, the differential pressure sensor 76 can include a single pressure sensing transducer or diaphragm that receives a first pressure on the first side 94 and a second pressure on the second side 96, and can provide an electrical signal that indicates the fluid level in the blood reservoir 72. In some embodiments, the differential pressure sensor 76 includes a first pressure sensing transducer or diaphragm at first side 94 and a second pressure sensing transducer or diaphragm at second side 96 and can provide one or more electrical signals that indicate the fluid level in the blood reservoir 72. In some embodiments, the differential pressure sensor 76 includes two pressure sensors in a package.

In some embodiments, the differential pressure sensor 76 can be disposable. In some embodiments, the differential pressure sensor 76 can be modeled after a disposable pressure sensor, such as Measurement Specialties 1620 model, which is a fully piezoresistive silicon pressure sensor for use in invasive blood pressure monitoring. The model 1620 can be used with automated assembly equipment and dropped directly into a disposable unit. Also, the model 1620 includes a dielectric gel placed over the sensor to provide electric and fluidic isolation and the model 1620 can be sterilized. In addition, the model 1620 has an operating product life of 168 hours and a shelf life of 5 years. In some embodiments, the differential pressure sensor 76 can be provided based on a micro-electromechanical system (MEMS) component, such as Measurement Specialties MS763 die.

The controller 78 can receive the at least one electrical signal from the differential pressure sensor 76 via communications path 102 and determine or calculate the fluid volume in the blood reservoir 72 based on the at least one electrical signal and the known geometric configuration of the blood reservoir 72. The controller 78 can provide at least one signal indicating at least one of: the fluid level in the blood reservoir 72 (a fluid level signal); and the fluid volume in the blood reservoir 72 (a fluid volume signal). In some embodiments, an HLM, such as the HLM 12 (shown in FIG. 1) or the HLM 54 (shown in FIG. 5A), can receive the at least one signal from the controller 78 and adjust an operating parameter of the HLM based on the at least one of the fluid level signal and the fluid volume signal. In some embodiments, a system, such as the DMS, can receive the at least one signal from the controller 78 and display at least one of the fluid level and the fluid volume in the blood reservoir 72.

While the controller 78 is shown as a distinct element and can be a standalone controller, in some embodiments, the controller 78 can be part of an HLM or part of a controller (similar to the controller 20) operating an HLM. Also, in some embodiments, the controller 78 can be part of the differential pressure sensor 76 or part of a display system, such as the DMS.

In operation of the blood reservoir system 70 with the blood reservoir 72 "open" as shown in FIG. 6, the first opening 86 is open to the atmosphere and the differential pressure sensor 76 can sense the hydrostatic pressure exerted on the first side 94 of the differential pressure sensor 76 by the fluid in the blood reservoir 72 and the atmospheric pressure exerted on the second side 96 of the differential pressure sensor 76, where the atmospheric pressure is the pressure exerted on the volume of fluid 80 from the air or atmosphere at 84 above the volume of fluid 80 in the blood reservoir 72. The differential pressure sensor 76 provides at least one electrical signal that indicates the fluid level in the blood reservoir 72. The controller 78 receives the at least one electrical signal from the differential pressure sensor 76 and determines the fluid volume in the blood reservoir 72 based on the at least one electrical signal and the known geometric configuration of the blood reservoir 72. The controller 78 provides at least one of a fluid level signal that indicates the fluid level in the blood reservoir 72 and a fluid volume signal that indicates the fluid volume in the blood reservoir 72.

In operation of the blood reservoir system 70 with the blood reservoir 72 "closed" as shown in FIG. 7, the first opening 86 is fluidically coupled to a vacuum and the second side 96 of the differential pressure sensor 76 is fluidically coupled to the air or other gas 84 above the volume of fluid 80 in the blood reservoir 72. The differential pressure sensor 76 can sense the hydrostatic pressure exerted on the first side 94 of the differential pressure sensor 76 by the fluid in the blood reservoir 72 and the pressure exerted on the volume of fluid 80 from the air or other gas 84 above the volume of fluid 80 via the tube 98 and the second side 96 of the differential pressure sensor 76. The differential pressure sensor 76 provides at least one electrical signal that indicates the fluid level in the blood reservoir 72. The controller 78 receives the at least one electrical signal from the differential pressure sensor 76 and determines the fluid volume in the blood reservoir 72 based on the at least one electrical signal and the known geometric configuration of the blood reservoir 72. The controller 78 provides at least one of a fluid level signal that indicates the fluid level in the blood reservoir 72 and a fluid volume signal that indicates the fluid volume in the blood reservoir 72.

Figure 8:
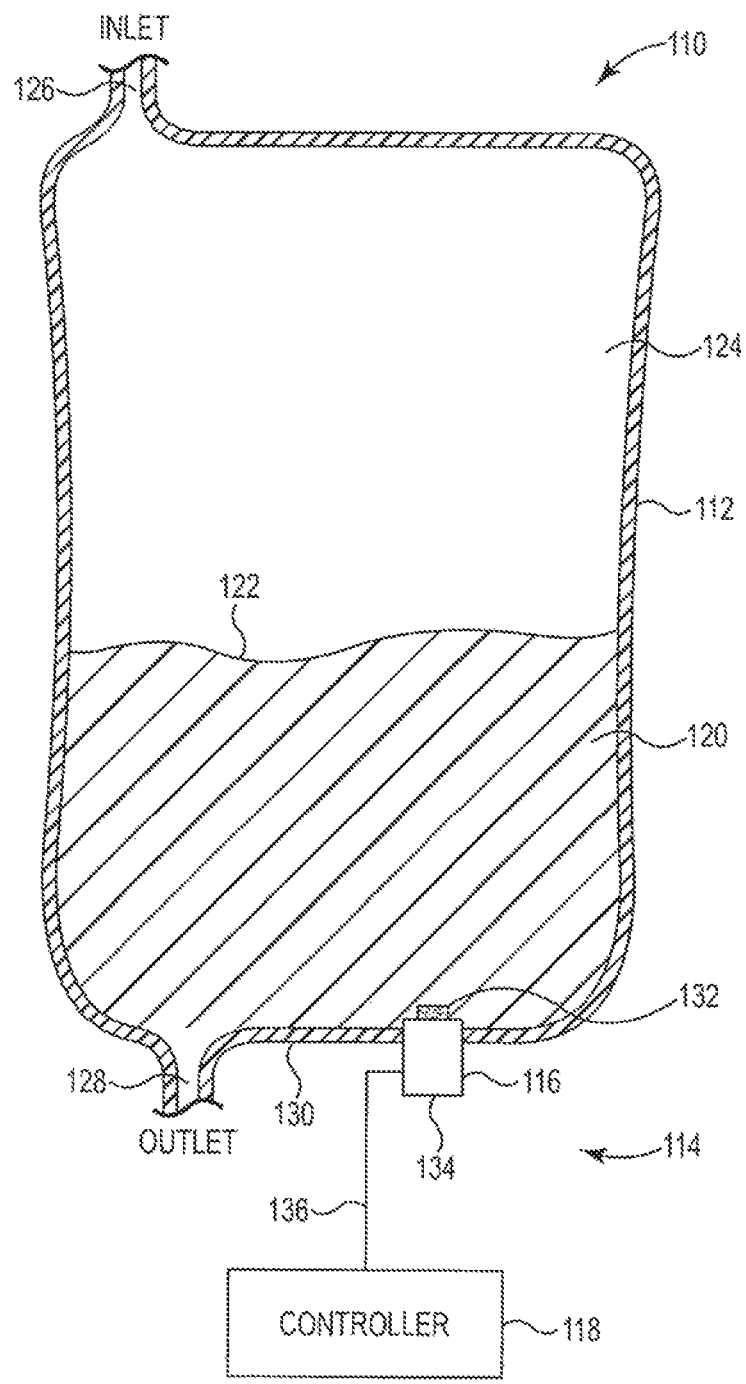
FIG. 8 is an illustration of a blood reservoir system that includes a differential pressure sensor and a soft shell blood reservoir.

FIG. 8 is an illustration of a blood reservoir system 110 that includes a soft shell blood reservoir 112 and a sensor system 114 that can be used in a perfusion system, such as the perfusion system 10 of FIG. 1 and the perfusion system 52 of FIG. 5A. The blood reservoir system 110 can also be used in an autotransfusion system, such as autotransfusion system 300 of FIG. 5B. The sensor system 114 includes a differential pressure sensor 116 and a controller 118. In some embodiments, the blood reservoir 112 can be similar to the blood reservoir 56. In some embodiments, the differential pressure sensor 116 can be similar to the fluid sensor 58. In some embodiments, the controller 118 can be similar to the controller 60.

The soft shell blood reservoir 112 is illustrated containing a volume of fluid 120, such as blood, that defines an interface 122 between the volume of fluid 120 and the air or other gas 124 in the space above the volume of fluid 120 in the blood reservoir 112. The blood reservoir 112 can include a first opening 126 that can be an inlet for the fluid and a second opening 128 that can be an outlet for the fluid. In some embodiments, the blood reservoir 112 can be a soft shell blood reservoir with a known geometry that can be based at least in part upon a known lateral expansion rate of the soft shell blood reservoir relative to the blood or fluid level within the blood reservoir 112.

The differential pressure sensor 116 can be located at the bottom 130 of the blood reservoir 112 to sense the pressure difference between the pressure exerted on the differential pressure sensor 116 by the fluid in the blood reservoir 112 and the pressure exerted on the soft shell blood reservoir 112, which is the atmospheric pressure. The differential pressure sensor 116 provides a signal that indicates the fluid level in the soft shell blood reservoir 112 and the controller 118 determines or calculates the fluid volume based on the fluid level and the known geometric configuration of the soft shell blood reservoir 112.

To sense the pressure difference, a first side 132 of the differential pressure sensor 116 can be in contact with the volume of fluid 120 in the blood reservoir 112 to sense the hydrostatic pressure exerted on the first side 132 of the differential pressure sensor 116 by the volume of fluid 120. A second side 134 of the differential pressure sensor 116 can be left open to the atmosphere to sense the atmospheric pressure.

The differential pressure sensor 116 can provide at least one electrical signal that correlates to the pressure difference and the pressures exerted on the first and second sides 132 and 134 of the differential pressure sensor 116, where the at least one electrical signal indicates the fluid level in the blood reservoir 112. In some embodiments, the differential pressure sensor 116 can provide at least one voltage signal that indicates the fluid level in the blood reservoir 112. In some embodiments, the differential pressure sensor 116 can provide the at least one electrical signal as a wired electrical signal(s). In some embodiments, the differential pressure sensor 116 can provide the at least one electrical signal as a wireless signal(s).

The differential pressure sensor 116 can be integrated into the blood reservoir 112. In some embodiments, the differential pressure sensor 116 can be snap fit into the bottom of the blood reservoir 112. In some embodiments, the differential pressure sensor 116 can be adhesively attached to the bottom of the blood reservoir 112. In some embodiments, the differential pressure sensor 116 can be molded into the blood reservoir 112, such that the differential pressure sensor 116 can be at least partially protected by the plastic material of the blood reservoir 112.

In some embodiments, the differential pressure sensor 116 can include a single pressure sensing transducer or diaphragm that receives a first pressure on the first side 132 and a second pressure on the second side 134, and can provide an electrical signal that indicates the fluid level in the blood reservoir 112. In some embodiments, the differential pressure sensor 116 includes a first pressure sensing transducer or diaphragm at first side 132 and a second pressure sensing transducer or diaphragm at second side 134 and can provide one or more electrical signals that indicate the fluid level in the blood reservoir 112. In some embodiments, the differential pressure sensor 116 includes two pressure sensors in a package.

In some embodiments, the differential pressure sensor 116 can be disposable. In some embodiments, the differential pressure sensor 116 can be modeled after a disposable pressure sensor, such as Measurement Specialties 1620 model, which is a fully piezoresistive silicon pressure sensor for use in invasive blood pressure monitoring. The model 1620 can be used with automated assembly equipment and dropped directly into a disposable unit. Also, the model 1620 includes a dielectric gel placed over the sensor to provide electric and fluidic isolation and the model 1620 can be sterilized. In addition, the model 1620 has an operating product life of 168 hours and a shelf life of 5 years. In some embodiments, the differential pressure sensor 116 can be provided based on a micro-electromechanical system (MEMS) component, such as Measurement Specialties MS763 die.

The controller 118 can receive the at least one electrical signal from the differential pressure sensor 116 via communications path 136 and determine or calculate the fluid volume in the blood reservoir 112 based on the at least one electrical signal and the known geometric configuration of the blood reservoir 112. The controller 118 can provide at least one signal indicating at least one of: the fluid level in the blood reservoir 112 (a fluid level signal); and the fluid volume in the blood reservoir 112 (a fluid volume signal). In some embodiments, an HLM, such as the HLM 12 (shown in FIG. 1) or the HLM 54 (shown in FIG. 5A), can receive the at least one signal from the controller 118 and adjust an operating parameter of the HLM based on the at least one of the fluid level signal and the fluid volume signal. In some embodiments, a system, such as the DMS, can receive the at least one signal from the controller 118 and display at least one of the fluid level and the fluid volume in the blood reservoir 112.

While the controller 118 is shown as a distinct element and can be a standalone controller, in some embodiments, the controller 118 can be part of an HLM or part of a controller (similar to the controller 20) operating an HLM. Also, in some embodiments, the controller 118 can be part of the differential pressure sensor 116 or part of a display system, such as the DMS.

In operation of the blood reservoir system 110 with the soft shell blood reservoir 112, the differential pressure sensor 116 can sense the hydrostatic pressure exerted on the first side 132 of the differential pressure sensor 116 by the fluid in the blood reservoir 112 and the atmospheric pressure exerted on the second side 134 of the differential pressure sensor 116, where the atmospheric pressure is the pressure exerted on the soft shell blood reservoir 112. The differential pressure sensor 116 provides at least one electrical signal that indicates the fluid level in the blood reservoir 112. The controller 118 receives the at least one electrical signal from the differential pressure sensor 116 and determines the fluid volume in the blood reservoir 112 based on the at least one electrical signal and the known geometric configuration of the blood reservoir 112. The controller 118 provides at least one of a fluid level signal that indicates the fluid level in the blood reservoir 112 and a fluid volume signal that indicates the fluid volume in the blood reservoir 112.

Figure 9:
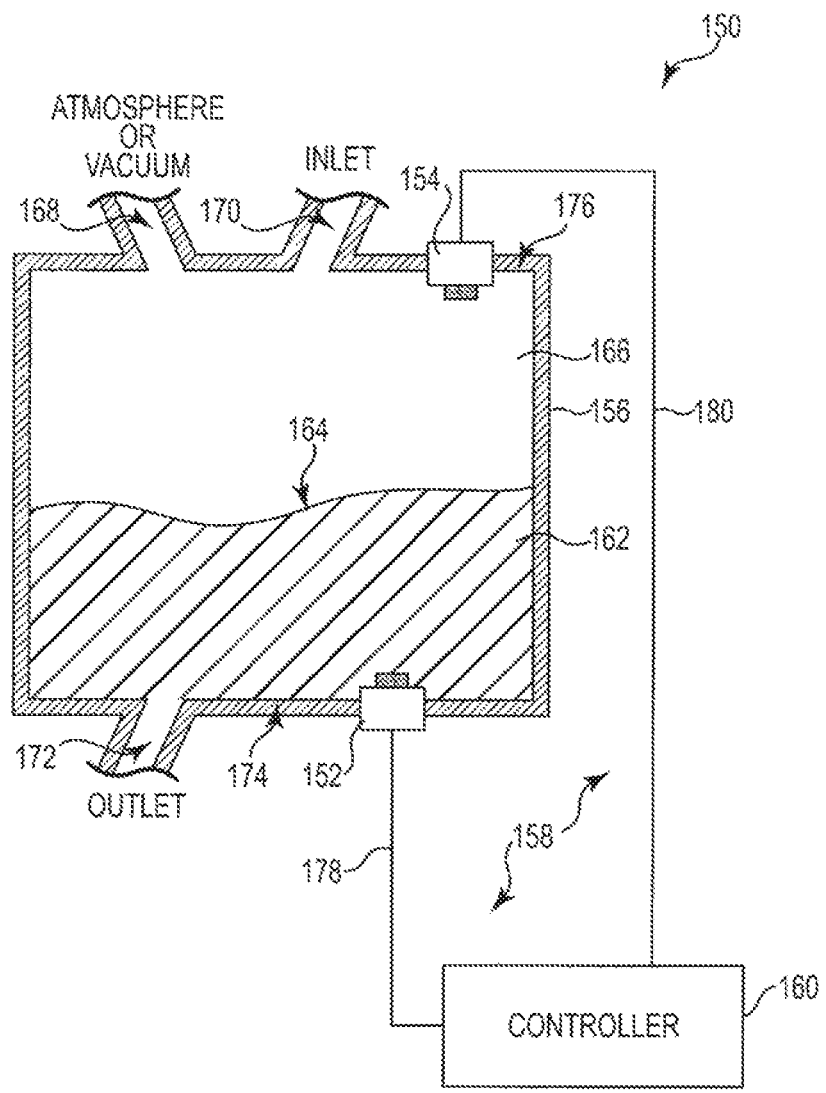
FIG. 9 is an illustration of a blood reservoir system that includes two separate pressure sensors and a hard shell blood reservoir.

FIG. 9 is an illustration of a blood reservoir system 150 that includes two separate pressure sensors, a first pressure sensor 152 and a second pressure sensor 154. The blood reservoir system 150 can be used in a perfusion system, such as the perfusion system 10 of FIG. 1 and the perfusion system 52 of FIG. 5A. The blood reservoir system 150 can also be used in an autotransfusion system, such as autotransfusion system 300 of FIG. 5B. The blood reservoir system 150 includes a blood reservoir 156 and a sensor system 158 that includes the first pressure sensor 152, the second pressure sensor 154, and a controller 160. The blood reservoir system 150 can be used with the blood reservoir 156 "open" to the atmosphere, such as when draining a patient by gravity, and with the blood reservoir 156 "closed" and fluidically coupled to a vacuum, such as when draining a patient with vacuum. In some embodiments, the blood reservoir 156 can be similar to the blood reservoir 56. In some embodiments, one or both of the first and second pressure sensors 152 and 154 can be similar to the fluid sensor 58. In some embodiments, the controller 160 can be similar to the controller 60.

The blood reservoir 156 is a rigid, hard shell blood reservoir illustrated containing a volume of fluid 162, such as blood, that defines an interface 164 between the volume of fluid 162 and the air or other gas 166 in the space above the volume of fluid 162 in the blood reservoir 156. The blood reservoir 156 can include a first opening 168 that can be left open to the atmosphere or fluidically coupled to a vacuum, a second opening 170 that can be an inlet for the fluid, and a third opening 172 that can be an outlet for the fluid. In some embodiments, the blood reservoir 156 can be a rigid, hard shell blood reservoir with a known geometry that can include the cross-sectional area of the blood reservoir 156, or a width and depth of the blood reservoir 156, as well as details on how the cross-sectional area varies relative to height within the blood reservoir 156.

The first pressure sensor 152 can be located at the bottom 174 of the blood reservoir 156 and in contact with the volume of fluid 162 to sense the hydrostatic pressure exerted on the first pressure sensor 152 by the fluid in the blood reservoir 156. The second pressure sensor 154 can be located at the top 176 of the blood reservoir 156 and in contact with the air or other gas 166 to sense the pressure exerted on the volume of fluid 162 above the fluid in the blood reservoir 156. In some embodiments, if the first opening 168 is open to the atmosphere, the second pressure sensor 154 can be left unattached to the blood reservoir 156 and open to the atmosphere to sense the atmospheric pressure, which is the pressure exerted on the volume of fluid 162 in the blood reservoir 156.

The fluid level in the blood reservoir 156 can be determined from the pressure difference between the pressure sensed by the first pressure sensor 152 and the pressure sensed by the second pressure sensor 154, and the fluid volume can be determined based on the fluid level and the known geometric configuration of the blood reservoir 156.

Each of the first and second pressure sensors 152 and 154 can provide at least one electrical signal, such as a voltage signal, that correlates to the pressure sensed by the pressure sensor, where the at least one electrical signal is proportional to or at least related to the fluid level and the fluid volume in the blood reservoir 156. In some embodiments, one or both of the first and second pressure sensors 152 and 154 can provide the at least one electrical signal as a wired electrical signal(s). In some embodiments, one or both of the first and second pressure sensors 152 and 154 can provide the at least one electrical signal as a wireless signal(s).

Also, each of the first and second pressure sensors 152 and 154 can be integrated into the blood reservoir 156. In some embodiments, one or both of the first and second pressure sensors 152 and 154 can be snap fit into the blood reservoir 156. In some embodiments, one or both of the first and second pressure sensors 152 and 154 can be adhesively attached to the blood reservoir 156. In some embodiments, one or both of the first and second pressure sensors 152 and 154 can be molded into the blood reservoir 156, such that only a connector may be accessible outside the blood reservoir 156 and the pressure sensor can be at least partially protected by the plastic material of the blood reservoir 156.

In some embodiments, one or both of the first and second pressure sensors 152 and 154 can be disposable. In some embodiments, one or both of the first and second pressure sensors 152 and 154 can be modeled after a disposable pressure sensor, such as Measurement Specialties 1620 model, which is a fully piezoresistive silicon pressure sensor for use in invasive blood pressure monitoring. The model 1620 can be used with automated assembly equipment and dropped directly into a disposable unit. Also, the model 1620 includes a dielectric gel placed over the sensor to provide electric and fluidic isolation and the model 1620 can be sterilized. In addition, the model 1620 has an operating product life of 168 hours and a shelf life of 5 years. In some embodiments, one or both of the first and second pressure sensors 152 and 154 can be provided based on a micro-electromechanical system (MEMS) component, such as Measurement Specialties MS763 die.

The controller 160 can receive the at least one electrical signal from each of the first and second pressure sensors 152 and 154 via communication paths 178 and 180, respectively. The controller 160 can determine or calculate at least one of a fluid level in the blood reservoir 156 and a fluid volume in the blood reservoir 156 based on the signals and the known geometry of the rigid, hard shell blood reservoir 156. The controller 160 can provide at least one signal indicating at least one of: the fluid level in the blood reservoir 156 (a fluid level signal); and the fluid volume in the blood reservoir 156 (a fluid volume signal). In some embodiments, an HLM, such as the HLM 12 (shown in FIG. 1) or the HLM 54 (shown in FIG. 5A), can receive the at least one signal from the controller 160 and adjust an operating parameter of the HLM based on the at least one of the fluid level signal and the fluid volume signal. In some embodiments, a system, such as the DMS, can receive the at least one signal from the controller 160 and display at least one of the fluid level and the fluid volume in the blood reservoir 156.

While the controller 160 is shown as a distinct element and can be a standalone controller, in some embodiments, the controller 160 can be part of an HLM or part of a controller (similar to the controller 20) operating an HLM. Also, in some embodiments, the controller 160 can be part of one or both of the first and second pressure sensors 152 and 154 or part of a display system, such as the DMS.

In operation of the blood reservoir system 150, with the blood reservoir 156 "open" and the first opening 158 open to the atmosphere, the first pressure sensor 152 can sense the hydrostatic pressure exerted on the first pressure sensor 152 by the fluid in the blood reservoir 156 and the second pressure sensor 154 can sense the atmospheric pressure exerted on the volume of fluid 152 in the blood reservoir 156. Next, each of the first and second pressure sensors 152 and 154 provides at least one electrical signal that indicates the pressure sensed by the pressure sensor. The controller 160 receives the signals from the first and second pressure sensors 152 and 154 and determines at least one of a fluid level in the blood reservoir 156 and a fluid volume in the blood reservoir 156 based on the received signals and the known geometry of the rigid, hard shell blood reservoir 156. The controller 160 provides at least one of a fluid level signal that indicates the fluid level in the blood reservoir 156 and a fluid volume signal that indicates the fluid volume in the blood reservoir 156.

In operation of the blood reservoir system 150, with the blood reservoir 156 "closed" and the first opening 168 fluidically coupled to a vacuum, the first pressure sensor 152 can sense the hydrostatic pressure exerted on the first pressure sensor 152 by the fluid in the blood reservoir 156 and the second pressure sensor 154 can sense the pressure exerted on the volume of fluid 162 above the volume of fluid 162 under vacuum. Next, each of the first and second pressure sensors 152 and 154 provides at least one electrical signal that indicates the pressure sensed by the pressure sensor. The controller 160 receives the signals from the first and second pressure sensors 152 and 154 and determines at least one of a fluid level in the blood reservoir 156 and a fluid volume in the blood reservoir 156 based on the received signals. The controller 160 provides at least one of a fluid level signal that indicates the fluid level in the blood reservoir 156 and a fluid volume signal that indicates the fluid volume in the blood reservoir 156.

Figure 10:
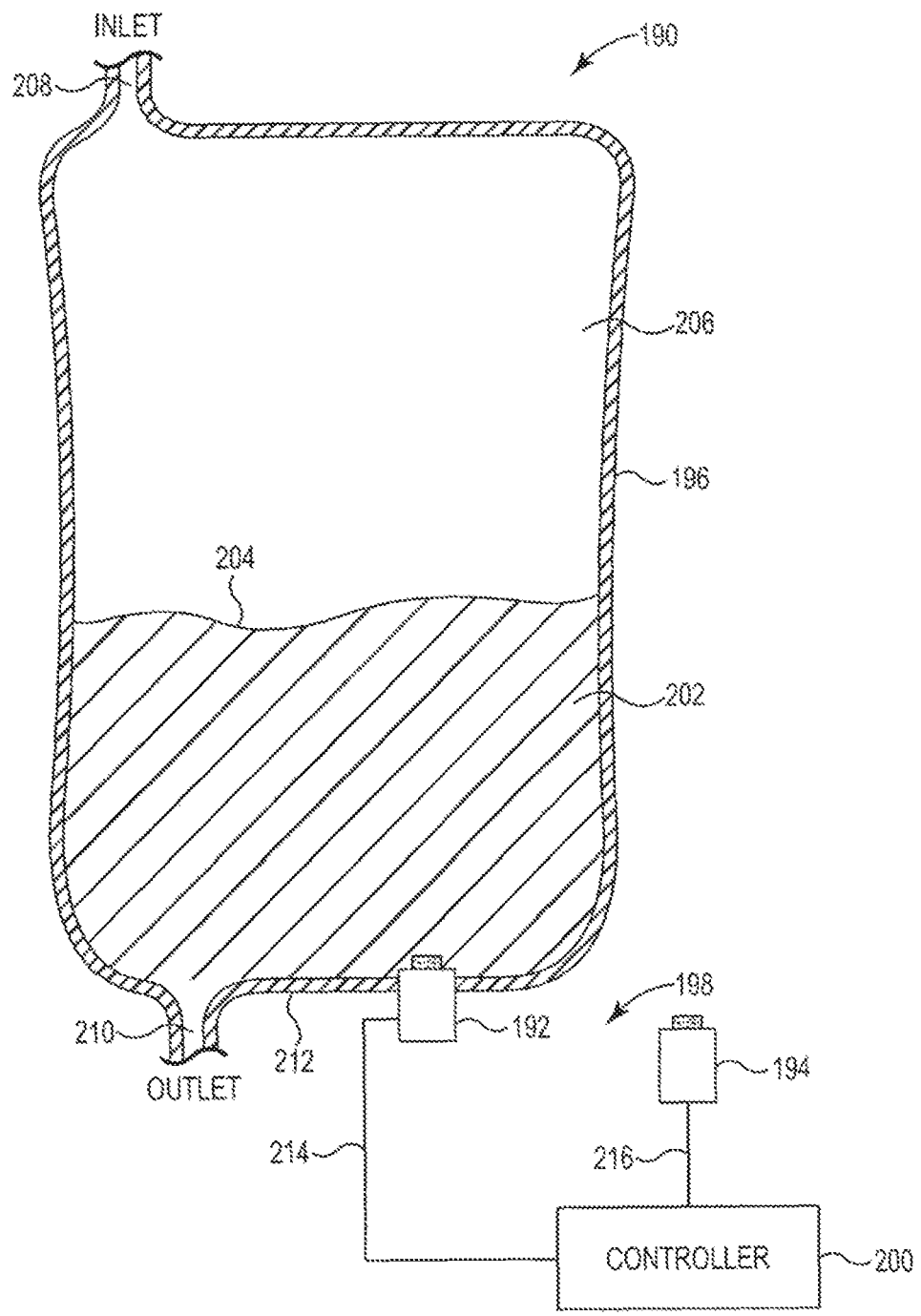
FIG. 10 is an illustration of a blood reservoir system that includes two separate pressure sensors and a soft shell blood reservoir.

FIG. 10 is an illustration of a blood reservoir system 190 that includes two separate pressure sensors, a first pressure sensor 192 and a second pressure sensor 194, and a soft shell blood reservoir 196. The blood reservoir system 190 can be used in a perfusion system, such as the perfusion system 10 of FIG. 1 and the perfusion system 52 of FIG. 5A. The blood reservoir system 190 can also be used in an autotransfusion system, such as autotransfusion system 300 of FIG. 5B. The blood reservoir system 190 includes the soft shell blood reservoir 196 and a sensor system 198 that includes the first pressure sensor 192, the second pressure sensor 194, and a controller 200. In some embodiments, the soft shell blood reservoir 196 can be similar to the blood reservoir 56. In some embodiments, one or both of the first and second pressure sensors 192 and 194 can be similar to the fluid sensor 58. In some embodiments, the controller 200 can be similar to the controller 60.

The soft shell blood reservoir 196 is illustrated containing a volume of fluid 202, such as blood, that defines an interface 204 between the volume of fluid 202 and the air or other gas 206 in the space above the volume of fluid 202 in the blood reservoir 196. The blood reservoir 196 can include a first opening 208 that can be an inlet for the fluid and a second opening 210 that can be an outlet for the fluid. In some embodiments, the blood reservoir 196 can be a soft shell blood reservoir with a known geometry that can be based at least in part upon a known lateral expansion rate of the soft shell blood reservoir relative to the blood or fluid level within the blood reservoir 196.

The first pressure sensor 192 can be located at the bottom 212 of the blood reservoir 196 and in contact with the volume of fluid 202 to sense the hydrostatic pressure exerted on the first pressure sensor 192 by the fluid in the blood reservoir 196. The second pressure sensor 194 can be left unattached to the blood reservoir 196 and open to the atmosphere to sense the atmospheric pressure, which is the pressure exerted on the soft shell blood reservoir 196.

The fluid level in the blood reservoir 196 can be determined from the pressure difference between the pressure sensed by the first pressure sensor 192 and the pressure sensed by the second pressure sensor 194, and the fluid volume can be determined based on the fluid level and the known geometric configuration of the blood reservoir 196.

Each of the first and second pressure sensors 192 and 194 can provide at least one electrical signal, such as a voltage signal, that correlates to the pressure sensed by the pressure sensor, where the at least one electrical signal is proportional to or at least related to the fluid level and the fluid volume in the blood reservoir 196. In some embodiments, one or both of the first and second pressure sensors 192 and 194 can provide the at least one electrical signal as a wired electrical signal(s). In some embodiments, one or both of the first and second pressure sensors 192 and 194 can provide the at least one electrical signal as a wireless signal(s).

Also, each of the first and second pressure sensors 192 and 194 can be integrated into the blood reservoir 196, with the second pressure sensor exposed to atmospheric pressure. In some embodiments, one or both of the first and second pressure sensors 192 and 194 can be snap fit into the blood reservoir 196. In some embodiments, one or both of the first and second pressure sensors 192 and 194 can be adhesively attached to the blood reservoir 196. In some embodiments, one or both of the first and second pressure sensors 192 and 194 can be molded into the blood reservoir 196.

In some embodiments, one or both of the first and second pressure sensors 192 and 194 can be disposable. In some embodiments, one or both of the first and second pressure sensors 192 and 194 can be modeled after a disposable pressure sensor, such as Measurement Specialties 1620 model, which is a fully piezoresistive silicon pressure sensor for use in invasive blood pressure monitoring. The model 1620 can be used with automated assembly equipment and dropped directly into a disposable unit. Also, the model 1620 includes a dielectric gel placed over the sensor to provide electric and fluidic isolation and the model 1620 can be sterilized. In addition, the model 1620 has an operating product life of 168 hours and a shelf life of 5 years. In some embodiments, one or both of the first and second pressure sensors 192 and 194 can be provided based on a microelectromechanical system (MEMS) component, such as Measurement Specialties MS763 die.

The controller 200 can receive the at least one electrical signal from each of the first and second pressure sensors 192 and 194 via communication paths 214 and 216, respectively. The controller 200 can determine or calculate at least one of a fluid level in the blood reservoir 196 and a fluid volume in the blood reservoir 196 based on the signals and the known geometry of the soft shell blood reservoir 196. The controller 200 can provide at least one signal indicating at least one of: the fluid level in the blood reservoir 196 (a fluid level signal); and the fluid volume in the blood reservoir 196 (a fluid volume signal). In some embodiments, an HLM, such as the HLM 12 (shown in FIG. 1) or the HLM 54 (shown in FIG. 5A), can receive the at least one signal from the controller 200 and adjust an operating parameter of the HLM based on the at least one of the fluid level signal and the fluid volume signal. In some embodiments, a system, such as the DMS, can receive the at least one signal from the controller 200 and display at least one of the fluid level and the fluid volume in the blood reservoir 196.

While the controller 200 is shown as a distinct element and can be a standalone controller, in some embodiments, the controller 200 can be part of an HLM or part of a controller (similar to the controller 20) operating an HLM. Also, in some embodiments, the controller 200 can be part of one or both of the first and second pressure sensors 192 and 194 or part of a display system, such as the DMS.

In operation of the blood reservoir system 190, the first pressure sensor 192 can sense the hydrostatic pressure exerted on the first pressure sensor 192 by the fluid in the blood reservoir 196 and the second pressure sensor 194 can sense the atmospheric pressure exerted on the volume of fluid 192 in the soft shell blood reservoir 196. Next, each of the first and second pressure sensors 192 and 194 provides at least one electrical signal that indicates the pressure sensed by the pressure sensor. The controller 200 receives the signals from the first and second pressure sensors 192 and 194 and determines at least one of a fluid level in the blood reservoir 196 and a fluid volume in the blood reservoir 196 based on the received signals and the known geometry of the soft shell blood reservoir 196. The controller 200 provides at least one of a fluid level signal that indicates the fluid level in the blood reservoir 196 and a fluid volume signal that indicates the fluid volume in the blood reservoir 196.

Figure 11:
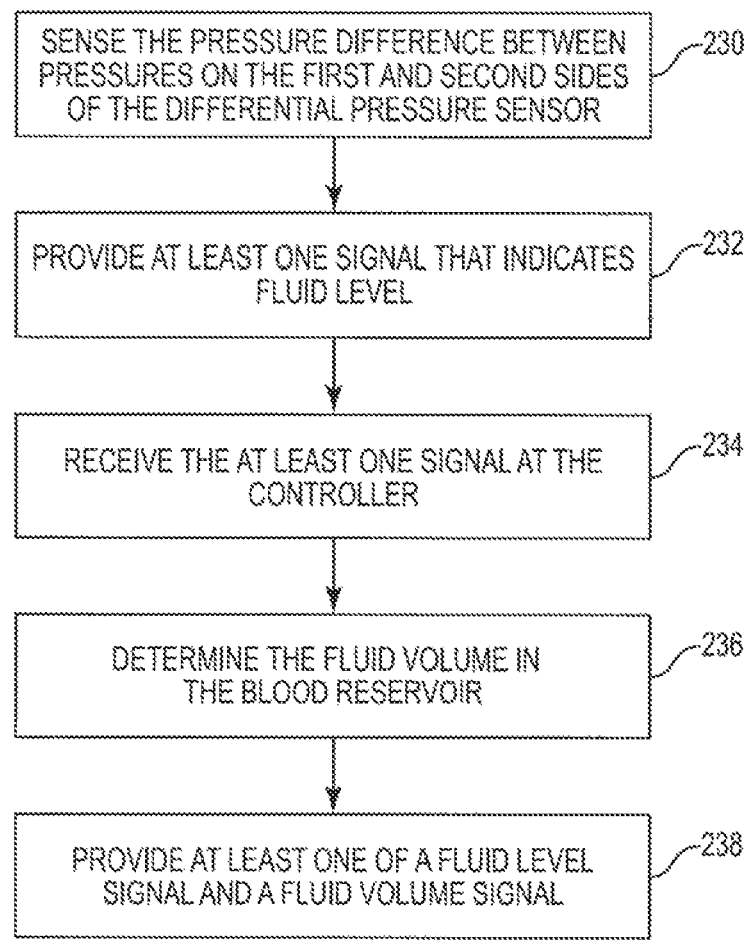
FIG. 11 is an illustration of a method of determining a fluid volume in the blood reservoir systems of FIGS. 6, 7, and 8.

FIG. 11 is an illustration of a method of determining the fluid volume in the blood reservoir system 70 of FIGS. 6 and 7 and in the blood reservoir system 110 of FIG. 8.

At 230, the differential pressure sensor senses the pressure difference between pressures on the first and second sides of the differential pressure sensor. The differential pressure sensor senses the pressure difference between the pressure exerted on the differential pressure sensor by fluid in the blood reservoir and the pressure exerted on the fluid in the blood reservoir.

At 232, the differential pressure sensor provides at least one signal that indicates the fluid level in the blood reservoir.

At 234, a controller receives the at least one signal from the differential pressure sensor and, at 236, the controller determines the fluid volume in the blood reservoir based on the at least one signal. At 238, the controller provides at least one of a fluid level signal that indicates the fluid level in the blood reservoir and a fluid volume signal that indicates the fluid volume in the blood reservoir.

Figure 12:
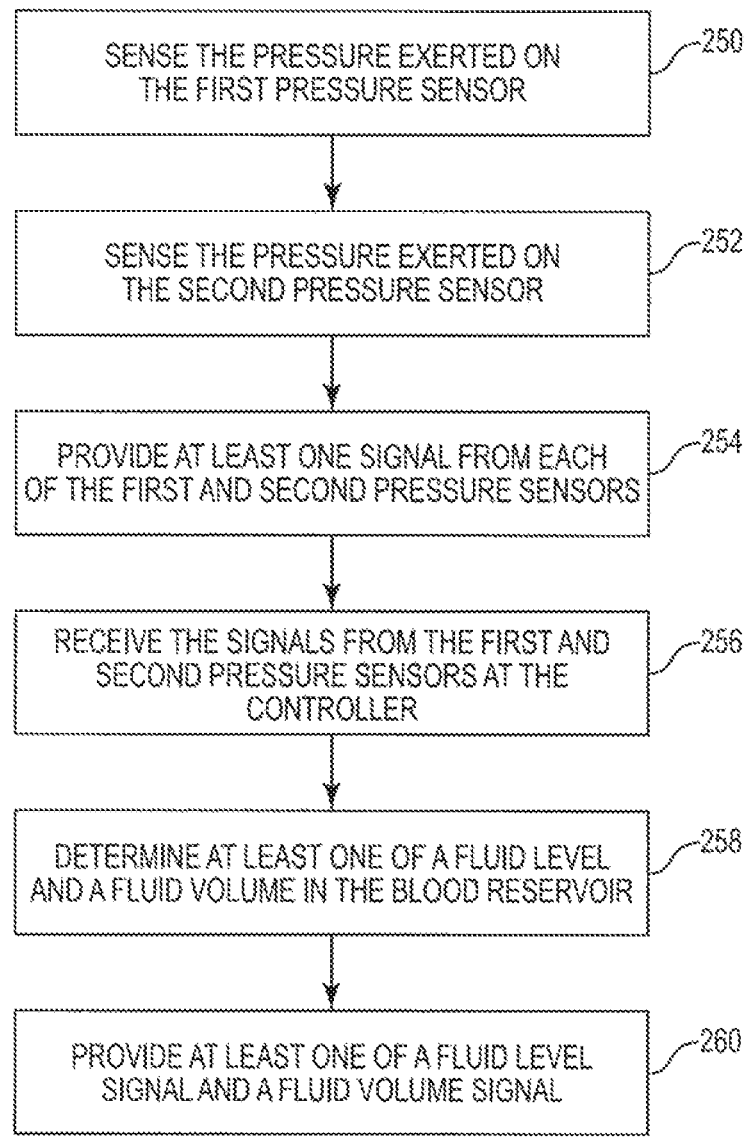
FIG. 12 is an illustration of a method of determining at least one of a fluid level and a fluid volume in the blood reservoir systems of FIGS. 9 and 10.

FIG. 12 is an illustration of a method of determining at least one of a fluid level and a fluid volume in the blood reservoir system 150 of FIG. 9 and in the blood reservoir system 190 of FIG. 10.

At 250, the first pressure sensor located at the bottom of the blood reservoir and in contact with the volume of fluid senses the hydrostatic pressure exerted on the first pressure sensor by the fluid in the blood reservoir. At 252, the second pressure sensor senses the pressure exerted on the volume of fluid in the blood reservoir.

At 254, each of the first and second pressure sensors provides at least one electrical signal that indicates or correlates to the pressure sensed by the pressure sensor.

At 256, the controller receives the signals from the first and second pressure sensors and, at 258, the controller determines at least one of a fluid level in the blood reservoir and a fluid volume in the blood reservoir based on the received signals. At 260, the controller provides at least one of a fluid level signal that indicates the fluid level in the blood reservoir and a fluid volume signal that indicates the fluid volume in the blood reservoir.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A system comprising:
a blood reservoir that is non-pressurized, the blood reservoir having a bottom and being configured to hold blood;
a differential pressure sensor integrated into the bottom of the blood reservoir and in contact with the blood in the blood reservoir to sense hydrostatic pressure of the blood in the blood reservoir and to sense a pressure difference between the hydrostatic pressure exerted on the differential pressure sensor by the blood and pressure exerted on the blood in the blood reservoir and to provide at least one signal that is indicative of a blood level in the blood reservoir; and
a controller to receive the at least one signal and calculate a blood level value and a blood volume value in the blood reservoir based on the at least one signal, the controller to provide at least one of a blood level signal that indicates the blood level in the blood reservoir and a blood volume signal that indicates the blood volume in the blood reservoir.

2. The system of claim 1, wherein the differential pressure sensor has a first side to sense the hydrostatic pressure exerted on the differential pressure sensor by the blood and a second side open to the atmosphere to sense atmospheric pressure.

3. The system of claim 1, wherein the differential pressure sensor has a first side to sense the hydrostatic pressure exerted on the differential pressure sensor by the blood and a second side fluidically coupled to the top of the blood reservoir to sense the pressure exerted on the blood in the blood reservoir.

4. The system of claim 1, wherein the differential pressure sensor includes a first sensor to sense the hydrostatic pressure exerted on the differential pressure sensor by the blood and a second sensor to sense the pressure exerted on the blood in the blood reservoir.

5. The system of claim 1, wherein the at least one of the blood level signal determining the blood level in the blood reservoir and the blood volume signal determining the blood volume in the blood reservoir is received by a heart lung machine that adjusts an operating parameter of the heart lung machine based on the at least one of the blood level signal that determines the blood level in the blood reservoir and the blood volume signal that determines the blood volume in the blood reservoir.

6. The system of claim 1, wherein the at least one of the blood level signal that determines the blood level in the blood reservoir and the blood volume signal that determines the blood volume in the blood reservoir is received by a display system that displays at least one of the blood level in the blood reservoir and the blood volume in the blood reservoir.

7. The system of claim 1, wherein the differential pressure sensor is one of snap fit and adhesively attached to the bottom of the blood reservoir.

8. The system of claim 1, wherein the differential pressure sensor is disposable.

9. The system of claim 1, wherein the controller is part of one of a heart lung machine and an autotransfusion system.

10. The system of claim 1, wherein the controller is part of a display system.

11. The system of claim 1, wherein the controller is part of the differential sensor.

12. A sensor system comprising:
a first pressure sensor integrated into a blood reservoir that is a non-pressurized blood reservoir, the blood reservoir holding blood and having a bottom, the first pressure sensor integrated into the bottom of the blood reservoir and in contact with the blood in the blood reservoir to sense hydrostatic pressure of the blood in the blood reservoir and to provide a first signal measuring the hydrostatic pressure exerted by the blood on the first pressure sensor;
a second pressure sensor to provide a second signal measuring pressure exerted on the blood in the blood reservoir; and
a controller to receive the first signal and the second signal and to determine at least one of a blood level in the blood reservoir and a blood volume in the blood reservoir based on the first signal and the second signal.

13. The sensor system of claim 12, wherein the second pressure sensor is open to the atmosphere to sense atmospheric pressure.

14. The sensor system of claim 12, wherein the second pressure sensor is coupled to the top of the blood reservoir to sense the pressure exerted on the blood in the blood reservoir.

15. The sensor system of claim 12, wherein the first pressure sensor and the second pressure sensor are part of a differential pressure sensor.

16. A method comprising:
providing a blood reservoir that is a non-pressurized blood reservoir, the blood reservoir having a bottom;
providing a differential pressure sensor integrated into the bottom of the blood reservoir and in contact with blood in the blood reservoir to sense hydrostatic pressure of the blood in the blood reservoir;
sensing, by the differential pressure sensor, the hydrostatic pressure of the blood in the blood reservoir and a pressure difference between the hydrostatic pressure exerted on the differential pressure sensor by the blood in the blood reservoir and pressure exerted on the blood in the blood reservoir;
providing, by the differential pressure sensor, at least one signal indicative of a level of the blood in the blood reservoir;
receiving the at least one signal at a controller;
determining, by the controller, a blood level and a blood volume in the blood reservoir based on the at least one signal; and
providing, by the controller, at least one of a blood level signal determining the blood level in the blood reservoir and a blood volume signal determining the blood volume in the blood reservoir.

17. The method of claim 16, wherein sensing comprises:
sensing the hydrostatic pressure exerted on the differential pressure sensor by the blood on a first side of the differential pressure sensor; and
sensing atmospheric pressure on a second side of the differential sensor.

18. The method of claim 16, wherein sensing comprises:
sensing the hydrostatic pressure exerted on the differential pressure sensor by the blood on a first side of the differential pressure sensor; and
sensing through fluidic coupling to the top of the blood reservoir the pressure exerted on the blood in the blood reservoir.

19. The method of claim 16, wherein sensing comprises:
sensing the hydrostatic pressure exerted on the differential pressure sensor by the blood via a first sensor; and
sensing the pressure exerted on the blood in the blood reservoir via a second sensor.

* * * * *